United States Patent
Nazzaro

(10) Patent No.: US 12,377,208 B2
(45) Date of Patent: Aug. 5, 2025

(54) SINGLE ACTUATED PRECISION DOSE INTERMEDIATE PUMPING CHAMBER

(71) Applicant: Insulet Corporation, Acton, MA (US)

(72) Inventor: David Nazzaro, Groveland, MA (US)

(73) Assignee: INSULET CORPORATION, Acton, MA (US)

( * ) Notice: Subject to any disclaimer, the term of this patent is extended or adjusted under 35 U.S.C. 154(b) by 775 days.

(21) Appl. No.: 17/569,572

(22) Filed: Jan. 6, 2022

(65) Prior Publication Data

US 2022/0218897 A1 Jul. 14, 2022

Related U.S. Application Data

(60) Provisional application No. 63/135,081, filed on Jan. 8, 2021.

(51) Int. Cl.
*A61M 5/142* (2006.01)
*A61M 5/145* (2006.01)

(52) U.S. Cl.
CPC ..... *A61M 5/14216* (2013.01); *A61M 5/14244* (2013.01); *A61M 5/1452* (2013.01); *A61M 2205/0266* (2013.01)

(58) Field of Classification Search
CPC ...... A61M 2025/0216; A61M 5/14244; A61M 5/16809; A61M 5/1452;
(Continued)

(56) References Cited

U.S. PATENT DOCUMENTS

| 1,441,508 A | 1/1923 | Jensen |
| 2,198,666 A | 4/1940 | Gruskin |

(Continued)

FOREIGN PATENT DOCUMENTS

| CA | 606281 A | 10/1960 |
| CN | 1375338 A | 10/2002 |

(Continued)

OTHER PUBLICATIONS

International Search Report and Written Opinion for PCT/US2018/014351, mailed on Jun. 4, 2018, 9 pages.

(Continued)

*Primary Examiner* — Michael J Tsai
*Assistant Examiner* — Justin L Zamory
(74) *Attorney, Agent, or Firm* — GOODWIN PROCTER LLP

(57) ABSTRACT

Disclosed are examples of devices, systems and techniques for delivering a liquid drug. An example delivery pump device may include a chamber body defining a pump chamber, an inlet valve to receive a liquid drug and a hard stop. A plunger configured with a plunger channel. A sliding fluidic member including a needle coupling, a flow orifice, a face seal and an anchor portion that may be movable within the pump chamber. A pump mechanism may be coupled to the anchor portion and operable to pull the anchor portion and the plunger toward the hard stop. Techniques may include determining a time to output a liquid drug from the delivery pump device; generating a control signal to actuate the delivery pump device; applying a control signal to the pump mechanism; determining that a control signal is to be removed from the pump mechanism; and delivering the liquid drug.

18 Claims, 14 Drawing Sheets

(58) Field of Classification Search
CPC ........... A61M 2205/0266; A61M 2005/14506; A61M 5/14216; A61M 2209/045; A61M 5/1456; F04B 9/02
See application file for complete search history.

(56) References Cited

U.S. PATENT DOCUMENTS

| | | |
|---|---|---|
| 2,752,918 A | 7/1956 | Uytenbogaar |
| 3,176,712 A | 4/1965 | Ramsden |
| 3,297,260 A | 1/1967 | Barlow |
| 3,464,359 A | 9/1969 | King |
| 3,885,662 A | 5/1975 | Schaefer |
| 3,946,732 A | 3/1976 | Hurscham |
| 3,947,692 A | 3/1976 | Payne |
| 3,993,061 A | 11/1976 | OLeary |
| 4,108,177 A | 8/1978 | Pistor |
| 4,152,098 A | 5/1979 | Moody et al. |
| 4,210,173 A | 7/1980 | Choksi et al. |
| 4,221,219 A | 9/1980 | Tucker |
| 4,257,324 A | 3/1981 | Stefansson et al. |
| 4,268,150 A | 5/1981 | Chen |
| 4,277,226 A | 7/1981 | Archibald |
| 4,313,439 A | 2/1982 | Babb et al. |
| 4,371,790 A | 2/1983 | Manning et al. |
| 4,417,889 A | 11/1983 | Choi |
| 4,424,720 A | 1/1984 | Bucchianeri |
| 4,435,173 A | 3/1984 | Siposs et al. |
| 4,475,905 A | 10/1984 | Himmelstrup |
| 4,498,843 A | 2/1985 | Schneider et al. |
| 4,507,115 A | 3/1985 | Kambara et al. |
| 4,551,134 A | 11/1985 | Slavik et al. |
| 4,562,751 A | 1/1986 | Nason et al. |
| 4,567,549 A | 1/1986 | Lemme |
| 4,585,439 A | 4/1986 | Michel |
| 4,601,707 A | 7/1986 | Albisser et al. |
| 4,634,427 A | 1/1987 | Hannula et al. |
| 4,671,429 A | 6/1987 | Spaanderman et al. |
| 4,678,408 A | 7/1987 | Nason et al. |
| 4,684,368 A | 8/1987 | Kenyon |
| 4,685,903 A | 8/1987 | Cable et al. |
| 4,755,169 A | 7/1988 | Sarnoff et al. |
| 4,766,889 A | 8/1988 | Trick et al. |
| 4,808,161 A | 2/1989 | Kamen |
| 4,846,797 A | 7/1989 | Howson et al. |
| 4,858,619 A | 8/1989 | Toth |
| 4,898,579 A | 2/1990 | Groshong et al. |
| 4,908,017 A | 3/1990 | Howson et al. |
| 4,944,659 A | 7/1990 | Labbe et al. |
| 4,969,874 A | 11/1990 | Michel et al. |
| 4,991,743 A | 2/1991 | Walker |
| 5,007,458 A | 4/1991 | Marcus et al. |
| 5,020,325 A | 6/1991 | Henault |
| 5,062,841 A | 11/1991 | Siegel |
| 5,147,311 A | 9/1992 | Pickhard |
| 5,178,609 A | 1/1993 | Ishikawa |
| 5,205,819 A | 4/1993 | Ross et al. |
| 5,213,483 A | 5/1993 | Flaherty et al. |
| 5,222,362 A | 6/1993 | Maus et al. |
| 5,236,416 A | 8/1993 | McDaniel et al. |
| 5,261,882 A | 11/1993 | Sealfon |
| 5,261,884 A | 11/1993 | Stern et al. |
| 5,277,338 A | 1/1994 | Divall et al. |
| 5,281,202 A | 1/1994 | Weber et al. |
| 5,346,476 A | 9/1994 | Elson |
| 5,364,342 A | 11/1994 | Beuchat et al. |
| 5,388,615 A | 2/1995 | Edlund et al. |
| 5,433,710 A | 7/1995 | VanAntwerp et al. |
| 5,503,628 A | 4/1996 | Fetters et al. |
| 5,520,661 A | 5/1996 | Lal et al. |
| 5,533,389 A | 7/1996 | Kamen et al. |
| 5,582,593 A | 12/1996 | Hultman |
| 5,618,269 A | 4/1997 | Jacobsen et al. |
| 5,628,309 A | 5/1997 | Brown |
| 5,637,095 A | 6/1997 | Nason et al. |
| 5,665,070 A | 9/1997 | McPhee |
| 5,713,875 A | 2/1998 | Tanner, II |
| 5,747,350 A | 5/1998 | Sattler |
| 5,748,827 A | 5/1998 | Holl et al. |
| 5,776,103 A | 7/1998 | Kriesel et al. |
| 5,779,676 A | 7/1998 | Kriesel et al. |
| 5,785,688 A | 7/1998 | Joshi et al. |
| 5,797,881 A | 8/1998 | Gadot |
| 5,800,397 A | 9/1998 | Wilson et al. |
| 5,807,075 A | 9/1998 | Jacobsen et al. |
| 5,839,467 A | 11/1998 | Saaski et al. |
| 5,891,097 A | 4/1999 | Saito et al. |
| 5,897,530 A | 4/1999 | Jackson |
| 5,906,597 A | 5/1999 | McPhee |
| 5,911,716 A | 6/1999 | Rake et al. |
| 5,919,167 A | 7/1999 | Mulhauser et al. |
| 5,957,890 A | 9/1999 | Mann et al. |
| 5,961,492 A | 10/1999 | Kriesel et al. |
| 5,971,963 A | 10/1999 | Choi |
| 6,019,747 A | 2/2000 | McPhee |
| 6,050,457 A | 4/2000 | Arnold et al. |
| 6,068,615 A | 5/2000 | Brown et al. |
| 6,159,188 A | 12/2000 | Laibovitz et al. |
| 6,174,300 B1 | 1/2001 | Kriesel et al. |
| 6,190,359 B1 | 2/2001 | Heruth |
| 6,200,293 B1 | 3/2001 | Kriesel et al. |
| 6,352,522 B1 | 3/2002 | Kim et al. |
| 6,363,609 B1 | 4/2002 | Pickren |
| 6,375,638 B2 | 4/2002 | Nason et al. |
| 6,474,219 B2 | 11/2002 | Klitmose et al. |
| 6,485,461 B1 | 11/2002 | Mason et al. |
| 6,485,462 B1 | 11/2002 | Kriesel |
| 6,488,652 B1 | 12/2002 | Weijand et al. |
| 6,520,936 B1 | 2/2003 | Mann |
| 6,527,744 B1 | 3/2003 | Kriesel et al. |
| 6,537,249 B2 | 3/2003 | Kriesell et al. |
| 6,539,286 B1 | 3/2003 | Jiang |
| 6,569,115 B1 | 5/2003 | Barker et al. |
| 6,595,956 B1 | 7/2003 | Gross et al. |
| 6,656,158 B2 | 12/2003 | Mahoney et al. |
| 6,699,218 B2 | 3/2004 | Flaherty et al. |
| 6,723,072 B2 | 4/2004 | Flaherty et al. |
| 6,740,059 B2 | 5/2004 | Flaherty |
| 6,749,407 B2 | 6/2004 | Xie et al. |
| 6,851,260 B2 | 2/2005 | Mernoe |
| 6,883,778 B1 | 4/2005 | Newton et al. |
| 7,018,360 B2 | 3/2006 | Flaherty et al. |
| 7,104,275 B2 | 9/2006 | Dille |
| 7,128,727 B2 | 10/2006 | Flaherty et al. |
| 7,137,964 B2 | 11/2006 | Flaherty |
| 7,160,272 B1 | 1/2007 | Eyal et al. |
| 7,303,549 B2 | 12/2007 | Flaherty |
| 7,771,392 B2 | 8/2010 | De Polo et al. |
| 7,914,499 B2 | 3/2011 | Gonnelli et al. |
| 7,951,114 B2 | 5/2011 | Rush et al. |
| 8,267,921 B2 | 9/2012 | Yodfat et al. |
| 8,382,703 B1 | 2/2013 | Abdelaal |
| 8,499,913 B2 | 8/2013 | Gunter |
| 8,905,995 B2 | 12/2014 | Mernoe |
| 8,920,376 B2 | 12/2014 | Caffey et al. |
| 8,939,935 B2 | 1/2015 | OConnor et al. |
| 9,180,244 B2 | 11/2015 | Anderson et al. |
| 9,192,716 B2 | 11/2015 | Jugl et al. |
| 9,402,950 B2 | 8/2016 | Dilanni et al. |
| 9,539,596 B2 | 1/2017 | Ikushima |
| 10,441,723 B2 * | 10/2019 | Nazzaro ............ A61M 5/1454 |
| 10,695,485 B2 | 6/2020 | Nazzaro |
| 2001/0016710 A1 | 8/2001 | Nason et al. |
| 2001/0056258 A1 | 12/2001 | Evans |
| 2002/0029018 A1 | 3/2002 | Jeffrey |
| 2002/0032374 A1 | 3/2002 | Holker et al. |
| 2002/0037221 A1 | 3/2002 | Mastrangelo et al. |
| 2002/0173769 A1 | 11/2002 | Gray et al. |
| 2002/0173830 A1 | 11/2002 | Starkweather et al. |
| 2003/0040715 A1 | 2/2003 | DAntonio et al. |
| 2003/0055380 A1 | 3/2003 | Flaherty |
| 2003/0097092 A1 | 5/2003 | Flaherty |
| 2003/0109827 A1 | 6/2003 | Lavi et al. |
| 2003/0163097 A1 | 8/2003 | Fleury et al. |
| 2003/0198558 A1 | 10/2003 | Nason et al. |

(56) References Cited

U.S. PATENT DOCUMENTS

| | | | |
|---|---|---|---|
| 2003/0199825 A1 | 10/2003 | Flaherty | |
| 2004/0010207 A1 | 1/2004 | Flaherty et al. | |
| 2004/0064088 A1 | 4/2004 | Gorman et al. | |
| 2004/0068224 A1 | 4/2004 | Couvillon, Jr. et al. | |
| 2004/0069044 A1 | 4/2004 | Lavi et al. | |
| 2004/0092865 A1 | 5/2004 | Flaherty et al. | |
| 2004/0094733 A1 | 5/2004 | Hower et al. | |
| 2004/0153032 A1 | 8/2004 | Garribotto et al. | |
| 2005/0020980 A1 | 1/2005 | Inoue et al. | |
| 2005/0165363 A1 | 7/2005 | Judson et al. | |
| 2005/0203461 A1 | 9/2005 | Flaherty et al. | |
| 2005/0238507 A1 | 10/2005 | Dilanni et al. | |
| 2005/0273059 A1 | 12/2005 | Mernoe | |
| 2005/0277882 A1 | 12/2005 | Kriesel | |
| 2006/0041229 A1 | 2/2006 | Garibotto et al. | |
| 2006/0079765 A1 | 4/2006 | Neer et al. | |
| 2006/0155210 A1 | 7/2006 | Beckman et al. | |
| 2006/0173439 A1 | 8/2006 | Thorne et al. | |
| 2006/0178633 A1 | 8/2006 | Garibotto et al. | |
| 2006/0253085 A1 | 11/2006 | Geismar et al. | |
| 2006/0282290 A1 | 12/2006 | Flaherty et al. | |
| 2007/0005018 A1 | 1/2007 | Tekbuchava | |
| 2007/0073236 A1 | 3/2007 | Merno et al. | |
| 2007/0088271 A1 | 4/2007 | Richards | |
| 2007/0118405 A1 | 5/2007 | Campbell et al. | |
| 2007/0282269 A1 | 12/2007 | Carter et al. | |
| 2008/0004515 A1 | 1/2008 | Jennewine | |
| 2008/0051738 A1 | 2/2008 | Griffin | |
| 2008/0114304 A1 | 5/2008 | Nalesso et al. | |
| 2008/0172028 A1 | 7/2008 | Blomquist | |
| 2008/0243211 A1 | 10/2008 | Cartwright et al. | |
| 2008/0294040 A1 | 11/2008 | Mohiuddin et al. | |
| 2009/0024083 A1 | 1/2009 | Kriesel et al. | |
| 2009/0062767 A1 | 3/2009 | Van Antwerp et al. | |
| 2009/0198215 A1 | 8/2009 | Chong et al. | |
| 2009/0278875 A1 | 11/2009 | Holm et al. | |
| 2009/0326472 A1 | 12/2009 | Carter et al. | |
| 2010/0036326 A1 | 2/2010 | Matusch | |
| 2010/0152658 A1 | 6/2010 | Hanson et al. | |
| 2010/0241066 A1 | 9/2010 | Hansen et al. | |
| 2010/0241076 A1 * | 9/2010 | Rush | F04B 49/065 604/151 |
| 2011/0054399 A1 | 3/2011 | Chong et al. | |
| 2011/0073620 A1 | 3/2011 | Verrilli | |
| 2011/0144586 A1 | 6/2011 | Michaud et al. | |
| 2011/0180480 A1 | 7/2011 | Kloeffel et al. | |
| 2011/0230833 A1 | 9/2011 | Landman et al. | |
| 2012/0078161 A1 | 3/2012 | Masterson et al. | |
| 2012/0172817 A1 | 7/2012 | Bruggemann et al. | |
| 2012/0209207 A1 | 8/2012 | Gray et al. | |
| 2013/0006213 A1 | 1/2013 | Arnitz et al. | |
| 2013/0017099 A1 | 1/2013 | Genoud | |
| 2013/0064701 A1 | 3/2013 | Konishi | |
| 2013/0177455 A1 | 7/2013 | Kamen et al. | |
| 2013/0178803 A1 | 7/2013 | Raab | |
| 2013/0245545 A1 | 9/2013 | Arnold et al. | |
| 2013/0267932 A1 | 10/2013 | Franke et al. | |
| 2013/0296792 A1 | 11/2013 | Cabiri | |
| 2014/0018730 A1 | 1/2014 | Muller-Pathle | |
| 2014/0127048 A1 | 5/2014 | Dilanni et al. | |
| 2014/0128839 A1 | 5/2014 | Dilanni et al. | |
| 2014/0142508 A1 | 5/2014 | Dilanni et al. | |
| 2014/0148784 A1 | 5/2014 | Anderson et al. | |
| 2014/0171901 A1 | 6/2014 | Langsdorf et al. | |
| 2015/0041498 A1 | 2/2015 | Kakiuchi et al. | |
| 2015/0051487 A1 | 2/2015 | Uber et al. | |
| 2015/0057613 A1 | 2/2015 | Clemente et al. | |
| 2015/0064036 A1 | 3/2015 | Eberhard | |
| 2015/0137017 A1 | 5/2015 | Ambrosina et al. | |
| 2015/0202386 A1 | 7/2015 | Brady et al. | |
| 2015/0290389 A1 | 10/2015 | Nessel | |
| 2015/0297825 A1 | 10/2015 | Focht et al. | |
| 2016/0008549 A1 | 1/2016 | Plumptre et al. | |
| 2016/0025544 A1 | 1/2016 | Kamer | |
| 2016/0055842 A1 | 2/2016 | Defranks et al. | |
| 2016/0082242 A1 | 3/2016 | Burton et al. | |
| 2016/0129190 A1 | 5/2016 | Haitsuka | |
| 2016/0193423 A1 | 7/2016 | Bilton | |
| 2016/0213851 A1 | 7/2016 | Weibel et al. | |
| 2017/0021096 A1 | 1/2017 | Cole et al. | |
| 2017/0021137 A1 | 1/2017 | Cole | |
| 2017/0100541 A1 | 4/2017 | Constantineau et al. | |
| 2017/0216516 A1 | 8/2017 | Dale | |
| 2017/0239415 A1 | 8/2017 | Hwang et al. | |
| 2017/0290975 A1 | 10/2017 | Barmaimon et al. | |
| 2018/0021521 A1 | 1/2018 | Sanchez | |
| 2018/0185579 A1 | 7/2018 | Joseph et al. | |
| 2018/0313346 A1 | 11/2018 | Oakes | |
| 2019/0192782 A1 | 6/2019 | Pedersen et al. | |
| 2019/0365993 A1 | 12/2019 | Staub et al. | |
| 2020/0009315 A1 | 1/2020 | Brouet et al. | |
| 2020/0345931 A1 | 11/2020 | Gray et al. | |

FOREIGN PATENT DOCUMENTS

| | | | |
|---|---|---|---|
| CN | 102498292 B | 7/2015 | |
| CN | 204972511 U | 1/2016 | |
| CN | 105764543 B | 7/2016 | |
| CN | 206175149 U | 5/2017 | |
| CN | 107096091 A | 8/2017 | |
| CN | 108472441 A | 8/2018 | |
| DE | 4200595 A1 | 7/1993 | |
| DE | 19723648 C1 | 8/1998 | |
| DE | 102005040344 A1 | 3/2007 | |
| EP | 0454331 A1 | 10/1991 | |
| EP | 0789146 A1 | 8/1997 | |
| EP | 867196 A2 | 9/1998 | |
| EP | 1065378 A2 | 1/2001 | |
| EP | 1177802 A1 | 2/2002 | |
| EP | 1403519 A1 | 3/2004 | |
| EP | 2397181 A1 | 12/2011 | |
| EP | 2468338 A1 | 6/2012 | |
| EP | 2703024 A1 | 3/2014 | |
| EP | 1874390 B1 | 10/2014 | |
| EP | 2830499 A1 | 2/2015 | |
| EP | 4059545 A1 * | 9/2022 | ............ A61M 39/08 |
| FR | 2096275 A5 | 2/1972 | |
| FR | 2455269 A1 | 11/1980 | |
| FR | 2507637 A1 | 12/1982 | |
| FR | 2731475 A1 | 9/1996 | |
| GB | 357139 A | 9/1931 | |
| GB | 810488 A | 3/1959 | |
| GB | 875034 A | 8/1961 | |
| GB | 1204836 A | 9/1970 | |
| GB | 2008806 A | 6/1979 | |
| GB | 2077367 A | 12/1981 | |
| GB | 2456681 A | 7/2009 | |
| GB | 2549750 A | 11/2017 | |
| IL | 46017 A | 11/1977 | |
| JP | 06063133 A | 3/1994 | |
| JP | 106296690 A | 10/1994 | |
| JP | H08238324 A | 9/1996 | |
| JP | 2004247271 A | 9/2004 | |
| JP | 2004274719 A | 9/2004 | |
| JP | 2005188355 A | 7/2005 | |
| JP | 2005-533545 A | 11/2005 | |
| JP | 2006159228 A | 6/2006 | |
| JP | 6098988 B2 | 9/2006 | |
| JP | 2006249130 A | 9/2006 | |
| JP | 2009514580 A | 4/2009 | |
| JP | 2015-134171 A | 7/2015 | |
| JP | 2017513577 A | 6/2017 | |
| NL | 1019126 C1 | 4/2003 | |
| WO | 8101658 A1 | 6/1981 | |
| WO | 8606796 A1 | 11/1986 | |
| WO | 9320864 A1 | 10/1993 | |
| WO | 9415660 A1 | 7/1994 | |
| WO | 9855073 A1 | 12/1998 | |
| WO | 9856293 A1 | 12/1998 | |
| WO | 9910040 A1 | 3/1999 | |
| WO | 9910049 A1 | 3/1999 | |
| WO | 9962576 A1 | 12/1999 | |
| WO | 0029047 A1 | 5/2000 | |
| WO | 0178812 A1 | 10/2001 | |

(56) References Cited

FOREIGN PATENT DOCUMENTS

| WO | 0220073 | A2 | 3/2002 | |
| WO | 0226282 | A2 | 4/2002 | |
| WO | 2002076535 | A1 | 4/2002 | |
| WO | 2003097133 | A1 | 4/2002 | |
| WO | 02068823 | A1 | 9/2002 | |
| WO | 2004032994 | A2 | 4/2004 | |
| WO | 2004056412 | A2 | 7/2004 | |
| WO | 2004110526 | A1 | 12/2004 | |
| WO | 2007066152 | A2 | 6/2007 | |
| WO | 2008133702 | A1 | 11/2008 | |
| WO | 2009039203 | A2 | 3/2009 | |
| WO | 2009141005 | A1 | 11/2009 | |
| WO | 2010022069 | A2 | 2/2010 | |
| WO | 2010077279 | A1 | 7/2010 | |
| WO | 2010139793 | A1 | 12/2010 | |
| WO | 2011010198 | A2 | 1/2011 | |
| WO | 2011031458 | A1 | 3/2011 | |
| WO | 2011069935 | A2 | 6/2011 | |
| WO | 2011075042 | A1 | 6/2011 | |
| WO | 2011133823 | A1 | 10/2011 | |
| WO | 2012073032 | A1 | 6/2012 | |
| WO | 2013050535 | A2 | 4/2013 | |
| WO | 2013137893 | A1 | 9/2013 | |
| WO | 2013149186 | A1 | 10/2013 | |
| WO | 2014029416 | A1 | 2/2014 | |
| WO | 2014149357 | A1 | 9/2014 | |
| WO | 2014179774 | A1 | 11/2014 | |
| WO | 2015032772 | A1 | 3/2015 | |
| WO | 2015048791 | A1 | 4/2015 | |
| WO | 2015081337 | A2 | 6/2015 | |
| WO | 2015117854 | A1 | 8/2015 | |
| WO | 2015167201 | A1 | 11/2015 | |
| WO | 2015177082 | A1 | 11/2015 | |
| WO | WO-2017139741 | A1 * | 8/2017 | ............ A61M 5/142 |
| WO | 2017148855 | A1 | 9/2017 | |
| WO | 2017187177 | A1 | 11/2017 | |
| WO | 2021016452 | A1 | 1/2021 | |

OTHER PUBLICATIONS

Lind et al. "Linear Motion Miniature Actuators." Paper presented at the 2nd Tampere International Conference on Machine Automation, Tampere, Finland (Sep. 1998).

Author Unknown "The Animas R-1000 Insulin Pump—Animas Corporation intends to exit the insulin pump businessand discontinue the manufacturing and sale of Animas® Vibe® and One Touch Ping® insulin pumps." [online], Dec. 1999 [retrieved on Jan. 8, 2019]. Retrieved from the Internet URL: http://www.animaspatientsupport.com/.

Author Unknown, CeramTec "Discover the Electro Ceramic Products CeramTec acquired from Morgan AdvancedMaterials" [online], Mar. 1, 2001 [retrieved on Jan. 8, 2019. Retrieved from the Internet URL: http://www.morgantechnicalceramics.com/.

Vaughan, M.E., "The Design, Fabrication, and Modeling of a Piezoelectric Linear Motor." Master's thesis, Virginia Polytechnic Institute and State University, VA. (2001).

Galante et al., "Design, Modeling, and Performance of a High Force Piezoelectric Inchworm Motor," Journal of Intelligent Material Systems and Structures, vol. 10, 962-972 (1999).

International Search Report and Written Opinion for International Application No. PCT/US2017/055054, mailed on Jan. 25, 2018, 13 pages.

International Search Report and Written Opinion for International Application No. PCT/US2018/045155, mailed on Oct. 15, 2018, 15 pages.

International Preliminary Report on Patentability for International Application No. PCT/US2017/034811 issued on Nov. 27, 2018, 10 pages.

International Preliminary Report on Patentability for International Patent Application No. PCT/US2017/046508, Feb. 12, 2019, 10 pages.

International Search Report and Written Opinion for International Application No. PCT/US2017/046508, mailed on Jan. 17, 2018, 14 pages.

International Search Report and Written Opinion for International Application No. PCT/US2017/046777, mailed on Dec. 13, 2017, 14 pages.

International Search Report and Written Opinion for International Application No. PCT/US2017/046737, mailed on Dec. 14, 2017, 11 pages.

International Search Report and Written Opinion for International Application No. PCT/US2017/034814, mailed on Oct. 11, 2017, 18 pages.

European Search Report and Written Opinion for the European Patent Application No. EP19177571, dated Oct. 30, 2019, 8 pages.

International Preliminary Report on Patentability for International Patent Application No. PCT/US2018/014351, dated Jul. 23, 2019, 7 pages.

International Preliminary Report on Patentability for International Patent Application No. PCT/US2017/046777, dated Feb. 19, 2019, 8 pages.

International Preliminary Report on Patentability for International Patent Application No. PCT/US2017/046737, dated Feb. 19, 2019, 8 pages.

International Preliminary Report on Patentability for International Patent Application No. PCT/US2017/055054, dated Apr. 9, 2019, 8 pages.

International Search Report and Written Opinion for Application No. PCT/US2017/034811, mailed Oct. 18, 2017, 15 pages.

EPO Search Report received in Application No. 13768938.6, dated Nov. 11, 2015, 8 pages.

International Search Report and Written Opinion for PCT Application No. PCT/US13/34674, mailed Aug. 6, 2013, 17 pages.

International Search Report and Written Opinion for International Application No. PCT/GB2007/004073, Jan. 31, 2008, 8 pages.

International Search Report and Written Opinion for International Patent Application No. PCT/US2019/063615, dated May 3, 2020, 17 pages.

International Preliminary Report on Patentability for International Patent Application No. PCT/US2018/045155, dated Feb. 14, 2020, 10 pages.

International Search Report and Written Opinion for International Patent Application No. PCT/US2019/035756, dated Jul. 31, 2019, 11 pages.

European Search Report and Written Opinion for European Patent Application No. EP20174878, dated Sep. 29, 2020, 4 pages.

Schott web-page image from Jul. 9, 2016, https://www.us.schott.com/pharmaceutical_packaging/english/products/cartridges.html.

International Search Report and Written Opinion for International Patent Application No. PCT/US2021/055581, dated Feb. 8, 2022, 19 pages.

International Search Report and Written Opinion for International Patent Application No. PCT/US2022/011356, dated Apr. 29, 2022, 19 pages.

International Search Report and Written Opinion for PCT Application No. PCT/US2019/059854, mailed Aug. 26, 2020, 15 pages.

International Search Report and Written Opinion, Application No. PCT/US2022/016713, mailed Aug. 5, 2022, 19 pages.

International Search Report and Written Opinion for International Patent Application No. PCT/US2022/029012, mailed Aug. 19, 2022, 12 pages.

* cited by examiner

SINGLE ACTUATED PRECISION DOSE INTERMEDIATE PUMPING CHAMBER

RELATED APPLICATIONS

This application claims the benefit of U.S. Provisional Patent Application No. 63/135,081, filed Jan. 8, 2021, the contents of which are incorporated herein by reference in their entirety.

TECHNICAL FIELD

The disclosed examples generally relate to medication delivery. More particularly, the disclosed examples relate to techniques, processes, systems, and pump devices for providing a fixed volume of fluid, which is delivered and refilled within one pumping cycle.

BACKGROUND

Many drug delivery devices include a reservoir for storing a liquid drug and a pump mechanism that is operated to expel the stored liquid drug from the reservoir for delivery to a user. The pump mechanism may be a positive displacement pump that pushes a dose of drug from a reservoir and through valving or shuttling to the patient. Other conventional pumps include, but are not limited to, diaphragm, rotary, vane, screw/turbine, or other types of conventional pumps. Some conventional drive mechanisms use a plunger to expel the liquid drug from the reservoir, which may result in a drive mechanism that generally has a length equal to a length of the reservoir.

The configurations of the various pump mechanisms may result in liquid drug doses to be nominally under- or over-delivered over time due to mechanical "sticking" or "slipping" of the pump mechanism.

Accordingly, there is a need for a simplified system for accurately expelling a liquid drug from a reservoir, which also reduces the overall size of a drug delivery device.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

In some approaches, a wearable drug delivery device that includes a reservoir and a delivery pump device is disclosed. The reservoir may be configured to store a liquid drug. The delivery pump device may be coupled to the reservoir for receiving the liquid drug from the reservoir. The delivery pump device may include a chamber body defining a pump chamber, an inlet port configured to enable a liquid drug from the reservoir to be drawn into the pump chamber, a sliding fluidic member including a flow orifice and a fluid pathway to a needle, a plunger including a plunger channel configured to be engaged with the sliding fluidic member, and a shape memory alloy wire coupled to the sliding fluidic member. The shape memory alloy wire is operable to draw the liquid drug from the reservoir through the inlet port and into the pump chamber by pulling the sliding fluidic member and the plunger in a first direction. The sliding fluidic member is configured to enable the liquid drug to be drawn into the pump chamber and expelled from the pump chamber into a fluid pathway to a needle for output.

In another aspect, a delivery pump device of a wearable drug delivery device is provided. The delivery pump device includes a chamber body, a plunger, a sliding fluidic member and a shape memory alloy. The chamber body defines a pump chamber and includes a hard stop and an inlet valve and operable to receive a liquid drug from a reservoir. The plunger may be movable within the pump chamber of the chamber body and configured with a plunger channel. The sliding fluidic member may be movable within the pump chamber and include a needle coupling, a flow orifice, a face seal and an anchor portion. The anchor portion is positioned and movable within the plunger channel in a leak-proof configuration. The shape memory alloy wire may be coupled to the anchor portion. The shape memory alloy wire is operable to pull the anchor portion and the plunger toward the hard stop.

In a further aspect, a method for controlling a delivery pump device to output a liquid drug is disclosed. The method includes determining a time to output a liquid drug from the delivery pump device. A control signal may be generated to actuate the delivery pump device. A control signal may be applied to a pump mechanism of the delivery pump device. The pump mechanism includes a shape memory alloy wire that is configured to respond to the applied control signal. As a pump chamber of the deliver pump device fills with the liquid drug, it is determined that the applied control signal is to be removed from the pump mechanism of the delivery pump device. The applied control signal may be removed from the pump mechanism to enable the liquid drug to be delivered from the pump chamber. Delivery of the liquid drug may be confirmed.

BRIEF DESCRIPTION OF THE DRAWINGS

In the drawings, like reference characters generally refer to the same parts throughout the different views. In the following description, various examples of the present disclosure are described with reference to the following drawings, in which.

The drawings are not necessarily to scale. The drawings are merely representations, not intended to portray specific parameters of the disclosure. The drawings are intended to depict examples of the disclosure, and therefore are not be considered as limiting in scope. Furthermore, certain elements in some of the figures may be omitted, or illustrated not-to-scale, for illustrative clarity. Still furthermore, for clarity, some reference numbers may be omitted in certain drawings.

DETAILED DESCRIPTION

Systems, devices, and methods in accordance with the present disclosure will now be described more fully hereinafter with reference to the accompanying drawings, where one or more examples are shown. The systems, devices, and methods may be embodied in many different forms and are not to be construed as being limited to the examples set forth herein. Instead, these examples are provided so the disclosure will be thorough and complete, and will fully convey the scope of methods and devices to those skilled in the art. Each of the systems, devices, and methods disclosed herein provides one or more advantages over conventional systems, components, and methods.

The pump mechanism described herein is intended to have the above advantageous characteristics. In addition, the pump mechanism is configured to output a set amount of a liquid drug during each "pulse" of the pump, which assumes that the displacing members of the pump mechanism travel from their "start" limits to their "stop" limits. The travel of the pump mechanism may be called the "pump stroke" and may have a variable distance of travel. In some examples, the pump stroke may be adjustable or may be a preset distance. A "pulse" may be considered as an actuation of the pump in response to a control signal during which a dose of liquid drug is output from the reservoir of the wearable drug delivery device.

Figure 1:
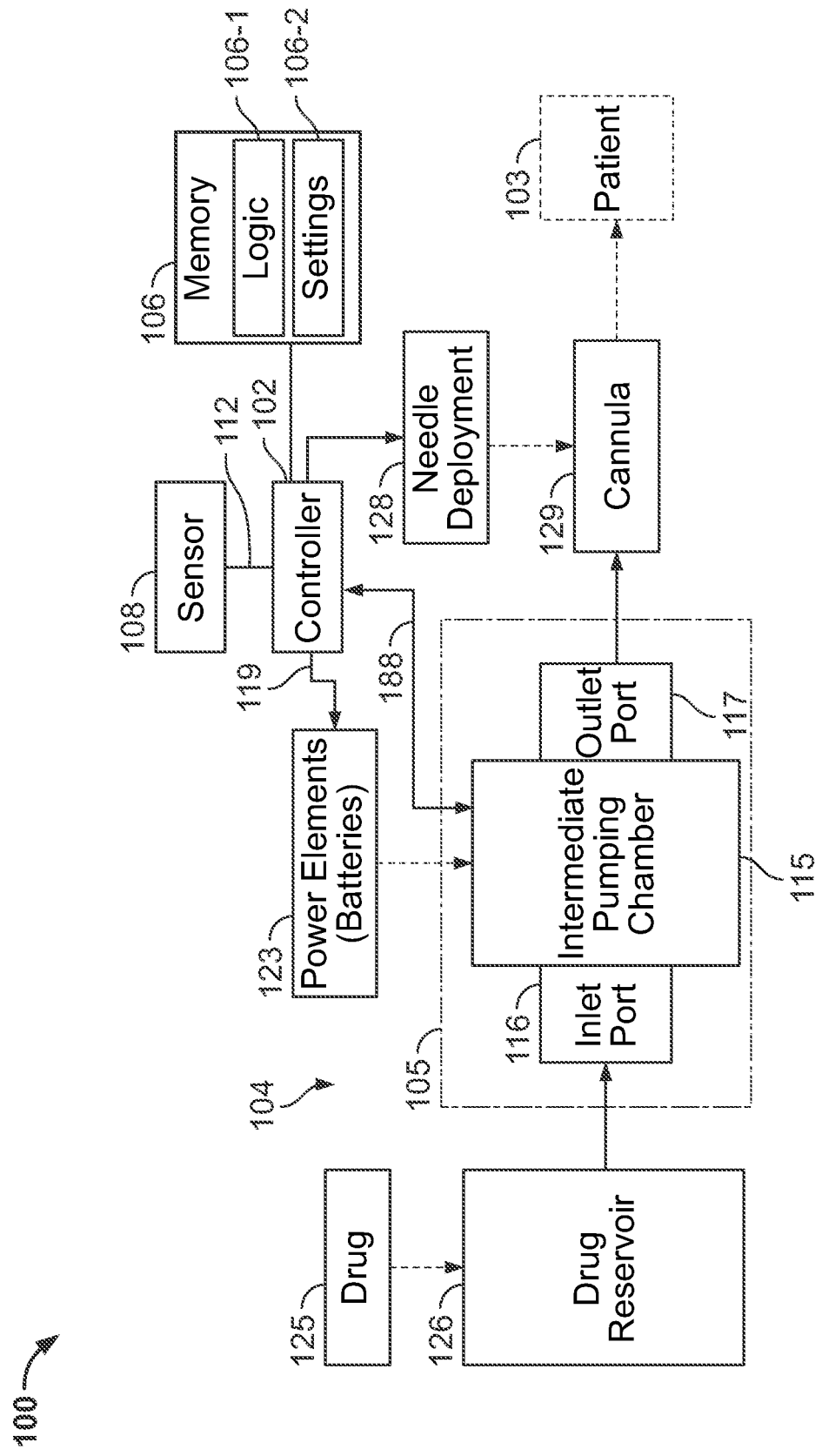
FIG. 1 illustrates a schematic diagram of a drug delivery system according to examples of the present disclosure.

FIG. 1 illustrates a simplified block diagram of an example system 100. The system 100 may be a wearable or on-body drug delivery device that is configured to be attached to the skin of a patient 103. The system 100 may include a controller 102, a pump mechanism 104 (also referred to as "pump 104"), and a sensor 108.

The sensor 108 may be an analyte sensor operable to detect ketones, lactates, uric acid, alcohol, glucose and the like. For example, the sensor 108 may be a glucose monitor such as, for example, a continuous glucose monitor. The sensor 108 may, for example, be operable to measure blood glucose (BG) values of a user to generate a measured BG level signal 112. The controller 102, the pump 104, and the sensor 108 may be communicatively coupled to one another via a wired or wireless communication path. For example, each of the controller 102, the pump 104 and the sensor 108 may be equipped with a wireless radio frequency transceiver operable to communicate via one or more communication protocols, such as Bluetooth®, or the like. As will be described in greater detail herein, the system 100 may also include a delivery pump device (also referred to as "device") 105, which includes a housing 114 defining an intermediate pumping chamber 115, an inlet port 116, and an outlet port 117. The system 100 may include additional components not shown or described for the sake of brevity.

In an example, the controller 102 may receive a desired BG level signal indicating a desired BG level or BG range for the patient 103. The desired BG level signal may be received from, for example, a user interface (not shown) to the controller 102 or another device, or by an algorithm that automatically determines an ideal BG level for the patient 103. The sensor 108 may be coupled to the patient 103 and operable to measure an approximate value of a BG level of the user. In response to the measured BG level or value, the sensor 108 may generate a signal indicating the measured BG value. As shown in the example, the controller 102 may also receive from the sensor 108 via a communication path, the measured BG level signal 112.

Based on the desired BG level signal and the measured BG level signal 112, the controller 102 may generate one or more control signals for directing operation of the pump 104. For example, one control signal 119 from the controller 102 may cause one or more power elements 123 operably connected with the device 105 to turn on or activate. As will be described with reference to the examples of FIGS. 2-13, the power element 123 may activate an SMA wire (not shown in this example) within the intermediate pumping chamber 115. In response, the SMA wire may change shape and/or length, which in turn may change a configuration of the intermediate pumping chamber 115.

An amount of a liquid drug 125 (e.g., insulin) may be drawn into the intermediate pumping chamber 115, through the inlet port 116, in response to a change in pressure due to the change in configuration of the intermediate pumping chamber 115. For example, the amount of the liquid drug 125 may be determined based on a difference between the desired BG level signal and the actual BG signal level 112. The amount of the liquid drug 125 may be determined as an appropriate amount of insulin to drive the measured BG level of the user to the desired BG level. Based on operation of the pump 104, as determined by the control signal 119, the patient 103 may receive the liquid drug from a reservoir 126 through a sequence of pulses. The system 100 may operate as a closed-loop system, an open-loop system, or as a hybrid system.

As further shown, the system 100 may include a needle deployment component 128 in communication with the controller 102. The needle deployment component 128 may include a needle/cannula 129 deployable into the patient 103. The cannula 129 may form a portion of a fluid path coupling the patient 103 to the reservoir 126.

As further shown, the outlet port 117 may be coupled to the cannula 129. The intermediate pumping chamber 115 via the outlet port 117 couple to a needle/cannula coupling (shown in another figure) that enables fluid from the reservoir 126 to be transferred to the cannula 129. The cannula 129 may be configured to allow fluid expelled from the device 105 to be provided to the patient 103.

The controller 102 may be implemented in hardware, software, or any combination thereof. The controller 102 may, for example, be a processor, a logic circuit or a microcontroller coupled to a memory 106. The memory 106 may include logic 106-1 and settings 106-2. The controller 102 may maintain a date and time and perform various functions (e.g., calculations or the like) that are usable to determine a status or state of various components of the system. The controller 102 may be operable to execute an algorithm such as an artificial pancreas (AP) algorithm stored in memory 106 as logic 106-1 that may be operable to enable the controller 102 to direct operation of the pump 104. The logic 106-1 may enable operation of the delivery device 105. For example, the controller 102 may be operable to receive an input from the sensor 108, wherein the input corresponds to an automated drug delivery, such as an automated insulin delivery (AID), application setting that the controller 102 may utilize in the control of the intermediate pumping chamber 115. Based on the AID application setting, the controller 102 may modify the behavior of the pump 104 and resulting amount of the liquid drug 125 to be delivered to the patient 103 via the device 105.

In some examples, the sensor 108 may be, for example, a continuous glucose monitor (CGM). The sensor 108 may be physically separate from the pump 104 or may be an integrated component within a same or an adjacent housing thereof. The sensor 108 may provide the controller 102 with data indicative of measured or detected blood glucose levels of the user.

The power element 123 may be a battery, a piezoelectric device, or the like, for supplying electrical power to the device 105. In other examples, the power element 123, or an additional power source (not shown), may also supply power to other components of the pump 104, such as the controller 102, the memory 106, the sensor 108, and/or the needle deployment component 128.

In an example, the sensor 108 may be a device communicatively coupled to the controller 102 and may be operable to measure a blood glucose value at a predetermined time interval, such as approximately every 5 minutes, 10 minutes, or the like. The sensor 108 may provide a number of blood glucose measurement values to an AP application executed by the controller 102 or by an external control device.

In some examples, the pump 104, when operating in a normal mode of operation, provides insulin stored in the reservoir 126 to the patient 103 based on information (e.g., blood glucose measurement values, target blood glucose values, insulin on board, prior insulin deliveries, time of day, day of the week, inputs from an inertial measurement unit, global positioning system-enabled devices, Wi-Fi-enabled devices, or the like) provided by the sensor 108 or other functional elements of the pump 104. For example, the pump 104 may contain analog and/or digital circuitry that may be implemented as the controller 102 for controlling the delivery of the drug or therapeutic agent. The circuitry used to implement the controller 102 may include discrete, specialized logic and/or components, an application-specific integrated circuit, a microcontroller or processor that executes software instructions, firmware, programming instructions or programming code enabling, for example, an AP application stored in memory 106, or any combination thereof. For example, the controller 102 may execute a control algorithm and other programming code, such as the AP application, that may make the controller 102 operable to cause the pump 104 to deliver doses of the drug or therapeutic agent to a user at predetermined intervals or as needed to bring blood glucose measurement values to a target blood glucose value or range. The size and/or timing of the doses may be pre-programmed, for example, into the AP application by the patient 103 or by a third party (such as a health care provider, a parent or guardian, a manufacturer of the wearable drug delivery device, or the like) using a wired or wireless link. The AP application may also be operable to automatically adjust any settings that may be pre-programmed (such as dosage limits for insulin, a number of strokes or pulses to deliver, and the like) based on data received from sensor 108 or detectors (shown in another figure) within the intermediate pumping chamber 115. The controller 102 may be coupled to the intermediate pumping chamber 115 via a communication path 188. The controller 102 may deliver control signals to components (shown in other examples) of the intermediate pumping chamber 115.

Although not shown, in some examples, the sensor 108 may include a processor, memory, a sensing or measuring device, and a communication device (not shown in this example). The memory may store an instance of an AP application as well as other programming code and be operable to store data related to the AP application.

In various examples, the sensing/measuring device of the sensor 108 may include one or more sensing elements, such as a blood glucose measurement element, a heart rate monitor, a blood oxygen sensor element, or the like. In an example, the sensor processor may include discrete, specialized logic and/or components, an application-specific integrated circuit, a microcontroller or processor that executes software instructions, firmware, programming instructions stored in memory, or any combination thereof.

Figure 2:
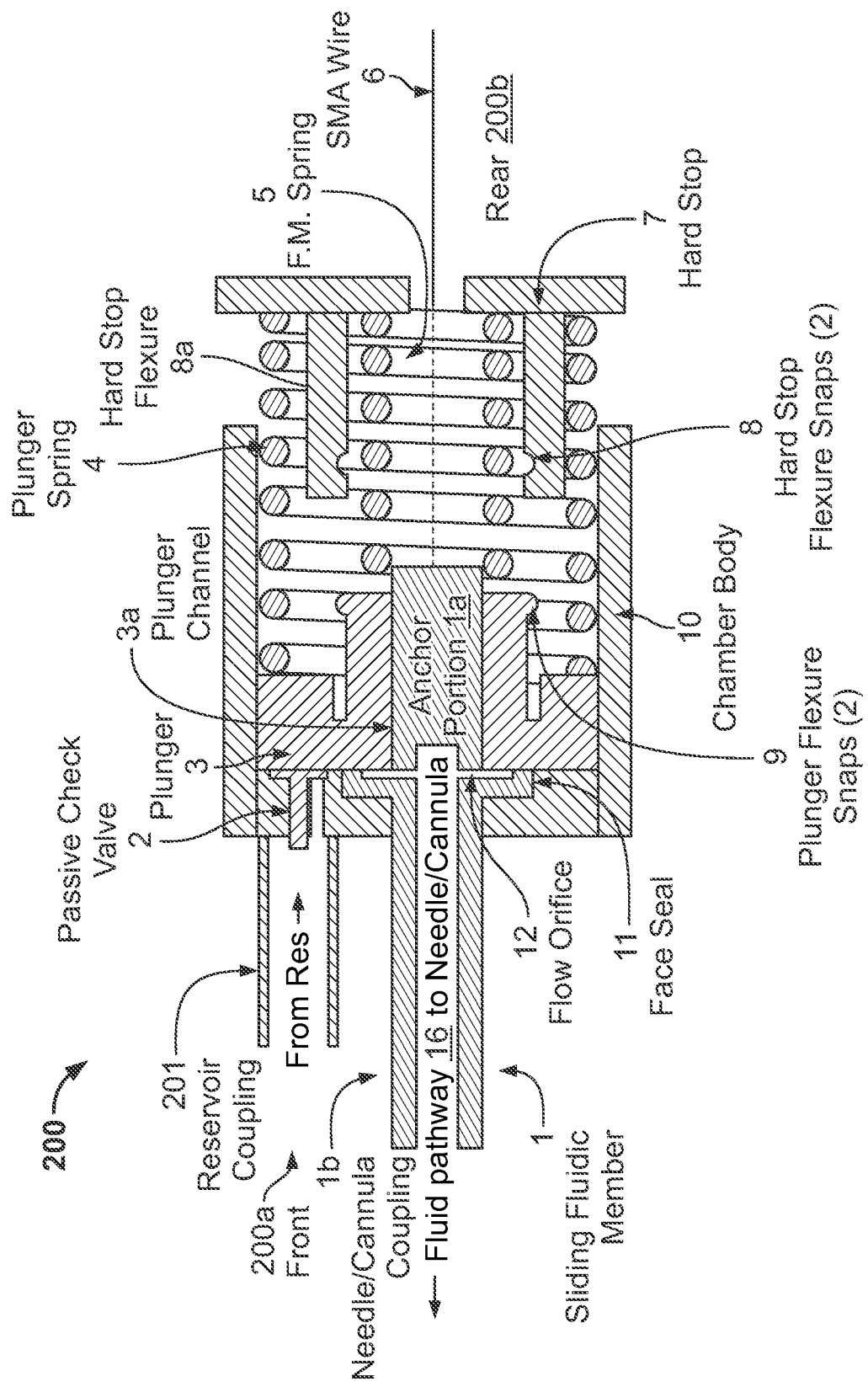
FIG. 2 illustrates a side cross-sectional view of an intermediate pumping chamber of the delivery pump device in an initial state of a pumping cycle.

FIG. 2 illustrates a side cross sectional view of the intermediate pumping chamber of the wearable drug delivery system example of FIG. 1 in an initial position. The intermediate pumping chamber 200 may have a front 200a and a back 200b and be coupled to a reservoir containing a liquid drug via reservoir coupling 201. The intermediate pumping chamber 200 may be operable to change configurations over the course of operation. For example, the initial position of FIG. 2 may be a position in which a liquid drug from the reservoir has not been pulled into the pump chamber (shown in more detail in another figure). Components of the example intermediate pumping chamber 200 may include sliding fluidic member 1, chamber body 10, and plunger 3. Additional components may include a valve 2, such as a passive check valve, a plunger spring 4, a fluidic member (FM) spring 5, a shape memory alloy (SMA) wire 6, a hard stop 7, and a face seal 11. The inlet port 116 of FIG. 1 may be formed by the passive check valve 2 and be configured to enable a liquid drug from the reservoir to be drawn into a pump chamber (shown in more detail in another figure). The plunger spring 4 and the FM spring 5 may be compression springs. The FM spring 5 and the plunger spring 4 are shown (in FIG. 2) in their rest position when the intermediate pumping chamber 200 is this initial position. Of course, other types of springs or other types of devices may be used in place of springs in the example intermediate pumping chamber 200.

In the example, the position of the sliding fluidic member 1 as shown in FIG. 2 may be considered a rest position or an initial position. The sliding fluidic member 1 may be configured with an anchor portion 1a, a needle/cannula coupling 1b, and a flow orifice 12. The needle/cannula coupling 1b may be configured, for example, as a hollow member, to provide a fluid pathway 16 to a needle/cannula (not shown in this example). The sliding fluidic member 1 may include a flow orifice 12 that is built into the sliding fluidic member 1 between the anchor portion 1a and the needle/cannula coupling 1b. For example, the sliding fluidic member 12 may include the flow orifice 12 and the fluid pathway 16 to a needle. The sliding fluidic member 1 may be coupled to the needle or cannula, such as 129 of FIG. 1. The anchor portion 1a may include structures (not shown for ease of illustration in this example) that connect the anchor portion 1a to the needle/cannula coupling 1b. The needle/cannula coupling 1b may be configured to remain coupled to the needle/cannula (not shown in this example) and extend into the chamber body 10. For example, the needle/cannula coupling 1b may be an elastic member, a multi-sectional, leak-proof, extendable tube, a combination thereof, or the like. The flow orifice 12 may be surrounded by structures that couple the needle/cannula coupling 1b to the anchor portion 1a but allow the liquid drug when in the pump chamber to enter the flow orifice 12 and flow in the fluid pathway 16 to the needle/cannula (shown in FIG. 1).

In the example intermediate pumping chamber 200, the passive check valve 2 may be configured to prevent backflow of the liquid drug when the pump chamber is filled with liquid drug (shown in a later example/figure) from the reservoir (shown in FIG. 1).

The plunger 3 may be configured to form a leakproof seal against the side of the chamber body 10. The plunger 3 as shown in later examples is operable to draw liquid drug from the reservoir and deliver the liquid drug through the fluid pathway 16 to the needle or cannula (not shown in this example). A surface of the plunger 3 facing the rear 200b of the intermediate pumping chamber 200 may be coupled to or sit against a plunger spring 4. The plunger spring 4 may, for example, be a compression spring that is shown at rest in FIG. 2. The end of the plunger spring 4 opposite the plunger 3 may couple to or rest against the hard stop 7.

In this example, the plunger 3 is configured with a plunger channel 3a and plunger flexure snap 9. The plunger channel 3a may be a hollow center portion in which fits an anchor portion 1a of the sliding fluidic member 1. The plunger channel 3a may be configured to surround the anchor portion 1a of the sliding fluidic member 1. The interface between the plunger channel 3a and the anchor portion 1a is leakproof, but the anchor portion 1a is configured to slide back and forth through the plunger channel 3a. The plunger flexure snaps 9 are flexible and may extend along a surface of the anchor portion 1a of the sliding fluidic member 1 and terminate with a bulbous portion (or in another embodiment, a concavity, or a portion complementary to the hard stop flexure snaps 8).

A face seal 11 may be disposed between the anchor portion 1a and the needle/cannula coupling 1b of the sliding fluidic member 1 and at a perimeter of the flow orifice 12. The face seal 11 may be operable to provide a leakproof seal of the flow orifice 12 that limits leakage of any liquid drug through or around a flow orifice 12 and into the fluid pathway 16 to the needle or cannula. The face seal 11 may be configured to prevent flow of the liquid drug to the patient while the intermediate pumping chamber is in the initial position. In some stages of operation, the face seal 11 may, for example, be under pressure from the plunger spring 4 of the intermediate pumping chamber 200 that prevents any liquid drug from entering the fluid pathway 16.

The SMA wire 6 may be nitinol or other known shape memory alloy wire that is operable to change length or shape in response to application of an electric current. For example, the SMA wire 6 may be coupled to a power source via circuitry that, when actuated in response to a control signal from a controller (such as shown in FIG. 1), is configured to apply a current or voltage to actuate the SMA wire 6.

The hard stop 7 may be configured to limit movement of the plunger 3. The hard stop 7 may be configured to include two hard stop flexures 8a that are configured to extend from the hard stop 7 toward the front 200a of the intermediate pumping chamber 200. In the example intermediate pumping chamber 200, each of the two hard stop flexures 8a may include hard stop flexure snap 8 at the end of the hard stop flexure 8a closest to the plunger 3. The hard stop flexure snaps 8 are, in this example, two flexible arm-like structures with inward facing concavities (or in another embodiment, protrusions, or a portion complementary to the plunger flexure snaps 9) at the respective ends of the flexible arm-like structures. While two hard stop flexure snaps 8 are shown, the number of hard stop flexure snaps 8 may be more or less, such as 1, 3, or 4, and may be utilized in other examples to engage more or less of the plunger flexure snaps 9 of the plunger 3. Interaction of the hard stop flexure snaps 8 and the plunger flexure snaps 9 are described in more detail with later examples.

Figure 3A:
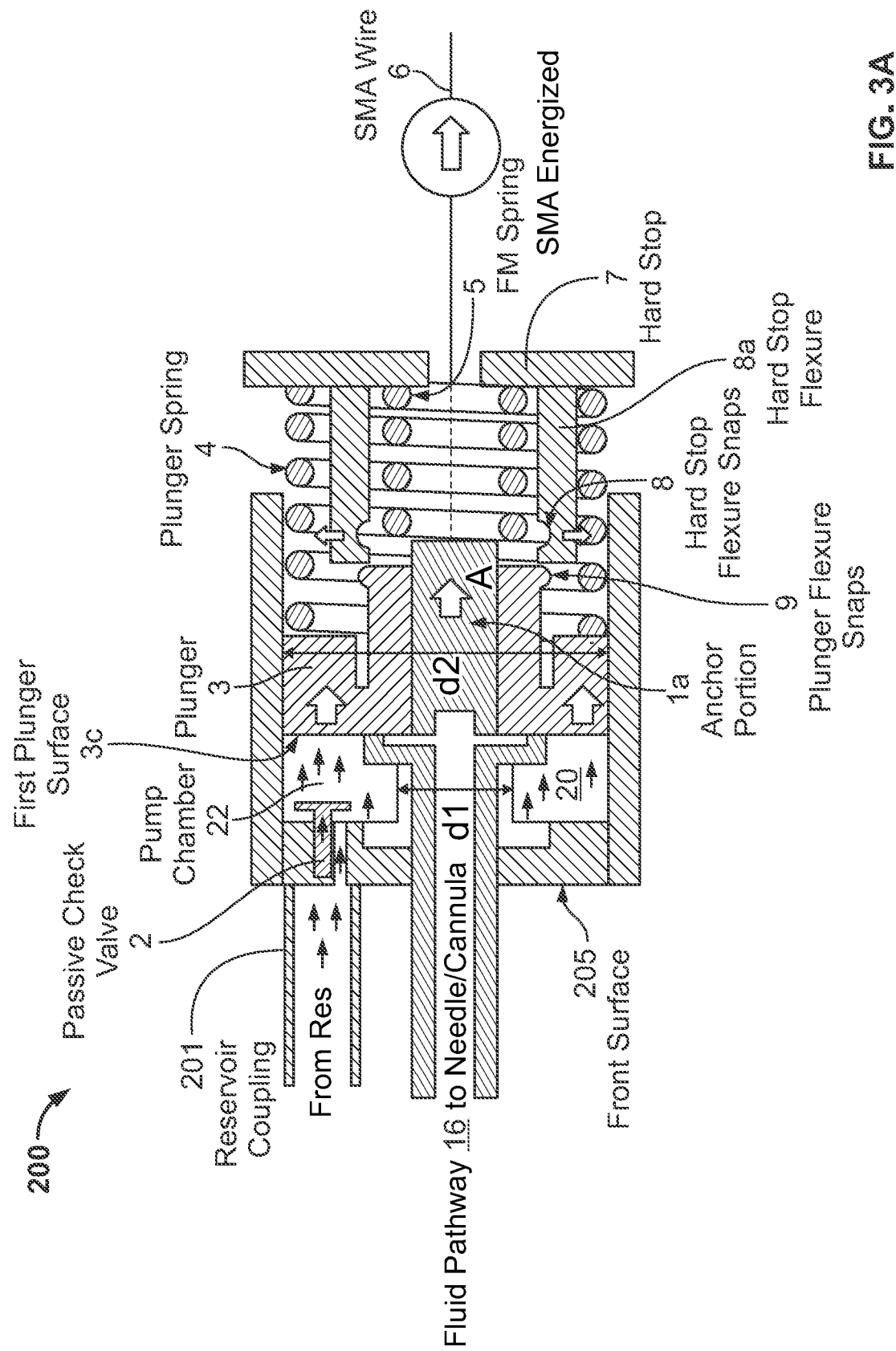
FIG. 3A illustrates a side cross-sectional views of an intermediate pumping chamber of the delivery pump device in transition from an initial state of a pumping cycle for the intermediate pumping chamber shown in the example of FIG. 2.

FIG. 3A illustrates a side cross-sectional view of the intermediate pumping chamber in transition from an initial position to a filled stage.

In FIG. 3A, the operation of the intermediate pumping chamber 200 is shown in response to the filling with liquid drug 20 from the reservoir via reservoir coupling 201. The SMA wire 6 is coupled to the anchor portion 1a and to circuitry (not shown in this example) responsive to signals from a controller (shown in an earlier example).

In response to being actuated, the SMA wire 6 may be pull on the anchor portion 1a of the sliding fluidic member 1 which pulls on the plunger 3 in the direction shown by the Arrow A. The pulling of the SMA wire 6 in the direction of Arrow A results in the sliding fluidic member 1 and the plunger 3 being pulled away from the front surface 205 of the intermediate pumping chamber 200 and away from the passive check valve 2. The pulling action of the SMA wire 6 on the anchor portion 1a creates a vacuum within the pump chamber 22. The vacuum causes the passive check valve 2 to open in the same direction as the sliding fluidic member 1 and plunger 3 are moving (as indicated by the unlabeled arrow on the passive check valve 2) and allows the pump chamber 22 to begin filling with liquid drug 20 from the reservoir via the reservoir coupling 201.

During this filling stage, the face seal 11 is asserted at a higher force (against a first plunger surface 3c of the plunger 3) on the flow orifice 12 due to compression of fluidic member spring 5 (e.g., F=−kx, where F is force, k is the spring constant and x is the distance the spring is compressed from its rest position). The position of hard stop 7 opposite from the front surface 205 of the intermediate pumping chamber 200 may be varied under tightly controlled conditions that permit adjustment of the pump stroke, or, alternatively, the position of the hard stop 7 may be factory configured for a preset pump stroke. The length of SMA wire 6 may configured based on the adjustment or setting of the pump stroke of the plunger and the position of the hard stop 7 to achieve the correct amount of pump stroke.

In the example of FIG. 3A, the plunger 3 and sliding fluidic member 1 are translating backwards toward the rear 200b of the intermediate pumping chamber 200. As the plunger 3 and the sliding fluidic members 1 are translating backwards, the hard stop flexures 8a and will interact. The plunger flexure snaps 9 are configured with semi-circular protrusions that when contacted by the hard stop flexure 8a cause the hard stop flexure 8a on both sides of the hard stop 7 to open toward the respective sides of the chamber body 10. As the hard stop flexure 8a separates the semicircular protrusions on the plunger flexure snaps 9 fill the hard stop flexure snaps 8, which are dimples in the hard stop flexure 8a of hard stop 7. This results in a two-way latch/snap that prevents the sliding fluidic member 1 and plunger 3 from translating further backwards toward the rear 200b of the intermediate pumping chamber 200.

Figure 3B:
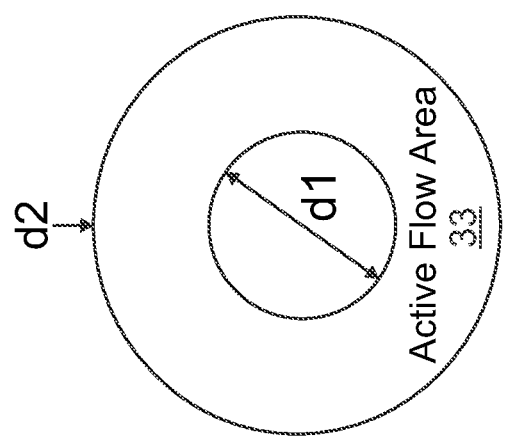
FIG. 3B illustrates an example fill area of an example pump chamber of an intermediate pumping chamber.

FIG. 3B illustrates an example of the active flow area of pump chamber in the example of FIG. 3A. As it is shown in the example of FIG. 3B, the active flow area 33 may be an annulus. An annular active flow area 33 enables larger components, such as a plunger 3, slidable fluidic member 1, and intermediate pumping chamber 10 to be used, which is favorable to component manufacturing and assembly. For example, the annular active flow 33 may be the result of using cylindrical structures (such a cylindrical plunger and cylindrical chamber body 10 (shown in an earlier example) and the like) that are easier to manufacture and assemble. Of course, other shapes such as ovular, rectangular, square, or the like may be used. For example, a ratio between d1 and d2 can be established such that dimensional control on the active flow area 33 section is achieved. This dimensional control facilitates increasing the scale of the size of the pump chamber and plunger size such that the manufacturing tolerance may be a small, or smaller, percentage of the actual size of the device 105. By controlling those dimensions d1 and d2, a desired pump chamber volume may be achieved. Given the small pump volumes, the larger the chamber and plunger become, the closer the chamber and plunger will become in nominal dimension. The approximate area of the active flow area 33 may be determined using the following the equation: $[(d2/2)2\times\pi]-[(d1/2)2\times\pi]-$(area of flow orifice 12 that extends beyond d1), where d2 is the diameter of the plunger 3 and d1 is the diameter of the sliding fluidic member 1.

Figure 4:
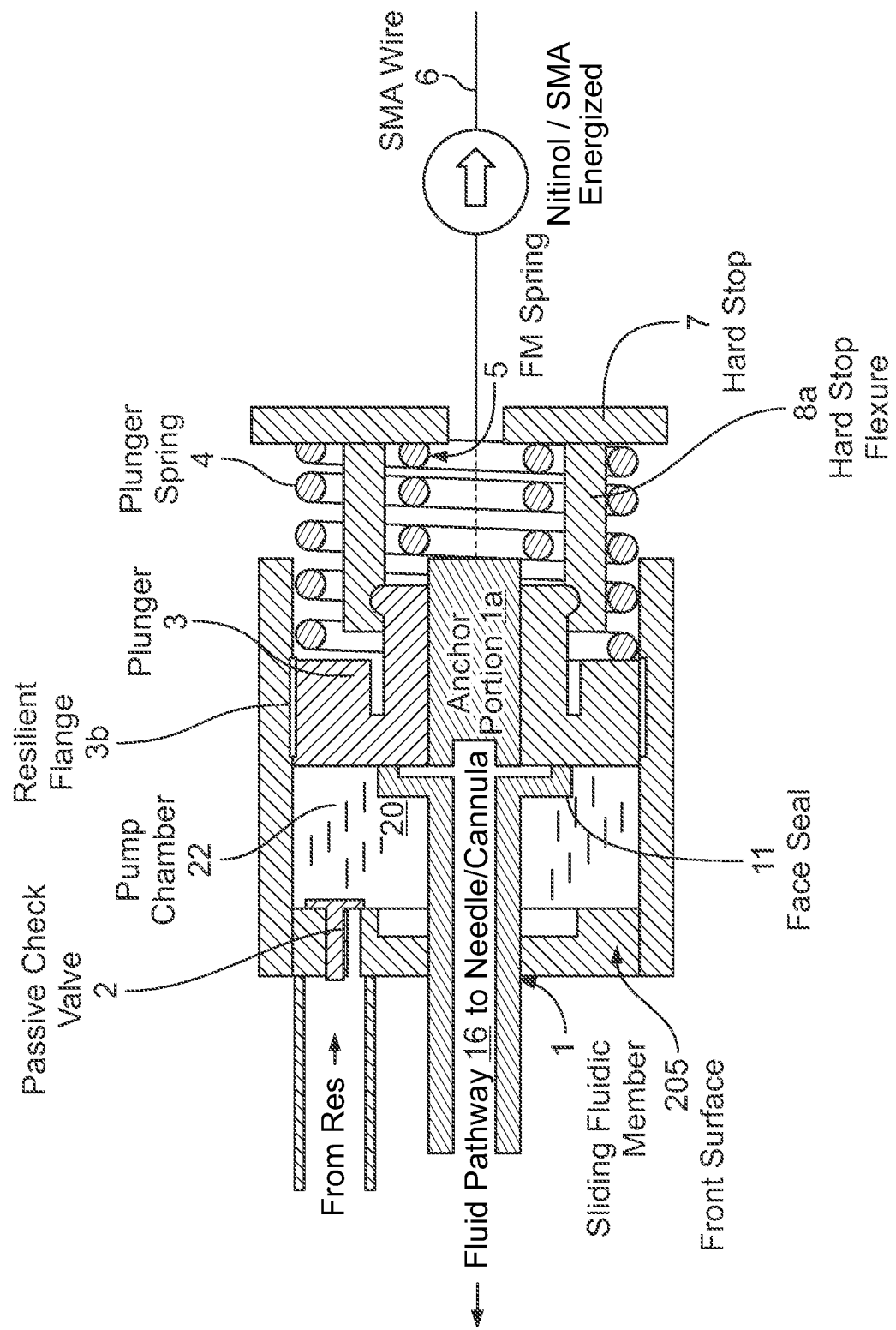
FIG. 4 illustrates a cross-sectional view of the example intermediate pumping chamber in a filled state prior to delivery of the liquid drug from the pump chamber.

In FIG. 4, the intermediate pumping chamber 200 has reached full stroke, the pump chamber 22 is full of liquid drug 20 and due to the pressure essentially returning to approximately 0 pounds per square inch gauge (psig), the passive check valve 2 has closed. Both plunger spring 4 and FM spring 5 are compressed and storing energy. In this example, the plunger flexure snaps 9 are operable to accomplish several actions, such as limiting travel of the plunger 3 within the intermediate pumping chamber 200 when drawing the liquid drug 20 from the reservoir (i.e., 126 of FIG. 1) into the pump chamber 22, assist the SMA wire 6 in maintaining the stored energy of the plunger spring 4 and the FM spring 5, preventing the plunger 3 from transitioning back toward the front surface 205 until the sliding fluidic member 1 has reached a specific point in its stroke, and the like. In some embodiments, plunger 3 may contact resilient flange 3b. Plunger 3 may contact one or more resilient flanges 3b. For instance, plunger 3 may contact a first resilient flange 3b at a top position relative to fluid pathway 16 and a second resilient flange 3b at a bottom position relative to fluid pathway 16. As explained further with reference to another figure, the plunger flexure snaps 9 and the hard stop flexure snaps 8 may provide electrical interfaces (e.g., electrical contacts or the like on each surface thereof) that when coupled to control circuitry are operable to confirm the pump chamber 22 is full or that delivery of the liquid drug has started. The position shown in FIG. 4 may be referred to as the full or loaded position.

Figure 5:
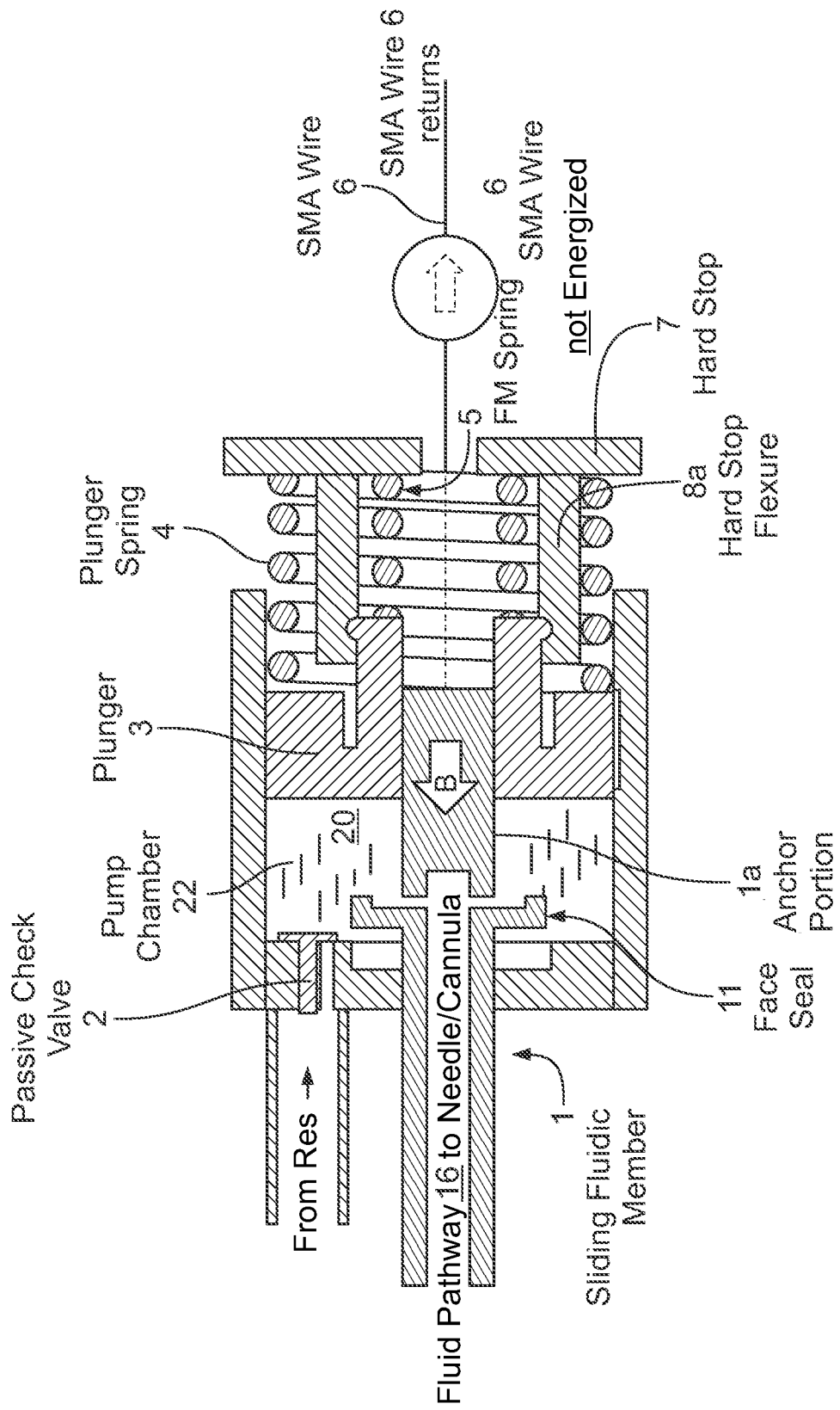
FIG. 5 illustrates a cross-sectional view of the example intermediate pumping chamber transitioning from the filled state of the example of FIG. 4 to delivery preparation state.

In FIG. 5, in response to current being released from the SMA wire 6, the SMA wire 6 is not energized and begins to return to its pre-actuation state. In addition, the FM spring 5 pushes (as shown by the arrow B) the sliding fluidic member 1 back toward the initial position shown in FIG. 2. Depending upon the configuration of the SMA wire 6 and the FM spring 5, the SMA wire 6 may serve as a brake on (and limit the force applied by) the FM spring 5 to slow the movement of the sliding fluidic member 1 in the direction of arrow B. Alternatively, the SMA wire 6 may be configured to allow the FM spring 5 to assert its full force on the sliding fluidic member 1.

As the sliding fluidic member 1 moves toward the front surface 205, the flow orifice 12 becomes exposed as the face seal 11 is no longer intact with the front surface of the plunger 3. In this example, the sliding fluidic member 1 can move within the space of the pump chamber 22 without displacing much, if any, liquid drug into the fluid pathway 16.

In addition, as the sliding fluidic member 1 moves toward the front surface 205, the plunger 3 remains stationary as the plunger flexure snaps 9 and hard stop flexure snaps 8 remain coupled due to support provided by the sliding fluidic member 1.

In the examples, when fully retracted into the plunger 3 (as shown in FIG. 3A) the anchor portion 1a of the sliding fluidic member 1 supports the plunger flexure snaps 9. The support provided by the sliding fluidic member 1 to the plunger flexure snaps 9 serves to keep the plunger flexure snaps 9 coupled with the hard stop flexure snaps 8.

However, as the sliding fluidic member 1 moves in the direction of arrow B in FIG. 5, the coupling between the plunger flexure snaps 9 and hard stop flexure snaps 8 becomes unstable.

Figure 6:
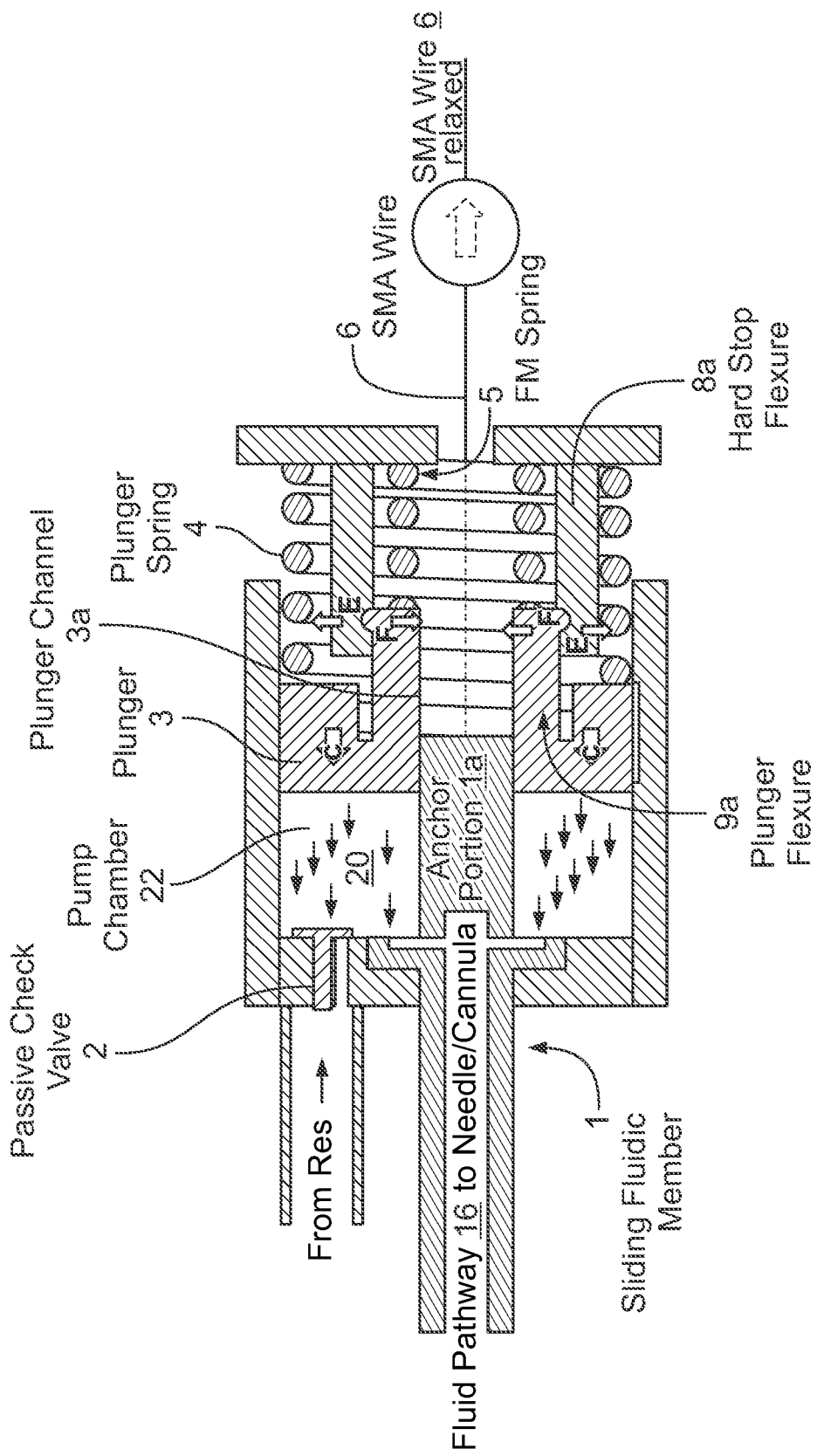
FIG. 6 illustrates a cross-sectional view of the example intermediate pumping chamber initiating delivery of the liquid drug from the pump chamber.

FIG. 6 illustrates the relaxing of the SMA wire 6 and the sliding fluidic member 1 is shown as having reached the forward limit of its travel due to hitting the inside of the front of the intermediate pumping chamber 200 in response to the force of the FM spring 5 against the anchor portion 1a.

Due to lack of support provided by the anchor portion 1a to the plunger flexures 9a, the plunger flexures 9a may be more prone to bending. As a result of the lack of support the hard stop flexures 8a do not need to bend as much to uncouple the respective plunger flexure snaps 9 and hard stop flexure snaps 8. The travel of the respective hard stop flexure snaps 8 and plunger flexure snaps 9 are shown by arrow E and arrow F. As shown in FIG. 6, the force asserted by plunger spring 4 on the plunger 3 causes the plunger 3 to move in the direction indicated by arrow C creating instability at the coupling of the respective plunger flexure snaps 9 and the hard stop flexure snaps 8. The instability allows the force of the plunger spring 4 to overcome the frictional forces that keep the plunger flexure snaps 9 and hard stop flexure snaps 8 coupled, the respective plunger flexures 9a and hard stop flexures 8a bend and thus release the plunger 3 for continued travel toward the front of the intermediate pumping chamber 200.

In a further example, the uncoupling of the plunger flexure snaps 9 and hard stop flexure snaps 8 also breaks the electrical connection formed by the coupled plunger flexure snaps 9 and hard stop flexure snaps 8, which a controller may interpret as delivery of the liquid drug to the fluid pathway 16 and to the user.

Figure 7:
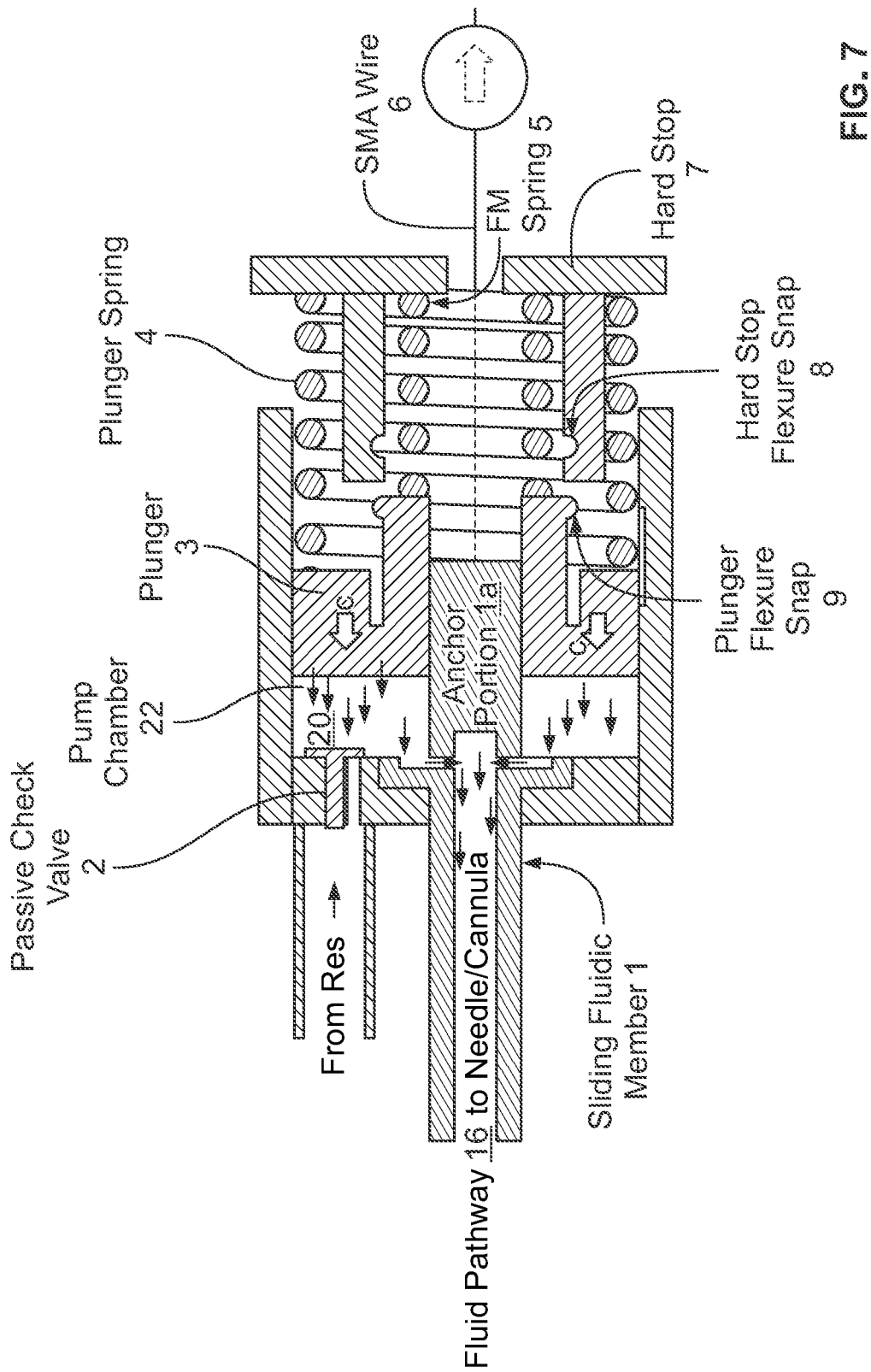
FIG. 7 illustrates a cross-sectional view of the example intermediate pumping chamber in a state in which movement of the plunger delivers the liquid drug from the pump chamber.

FIG. 7 illustrates movement of the plunger to deliver the liquid drug from the pump chamber 22. In the example of FIG. 7, the plunger 3 is shown collapsing the pump chamber 22 under the force of the plunger spring 4 and expelling the liquid drug 20 of the pump chamber 22 out the exit orifice 12. The passive check valve 2 is closed under the pressure of the liquid drug 20 and keeps any liquid drug 20 from returning to the reservoir. The pump flow rate Q, is a factor of spring rate and flow orifice diameter/length and pipe dimensions to the patient, best described by Poiseuille's law, as follows:

| | |
|---|---|
| Q | Flow rate |
| P | Pressure |
| r | Radius |
| η | Fluid viscosity |
| l | Length of tubing |

$$Q = \frac{\pi P r^4}{8 \eta l}$$

When the pump chamber 22 is fully collapsed under the force of the plunger spring 4, the intermediate pumping chamber 200 is returned to its initial position as shown in FIG. 2 with the intermediate pumping chamber 200 at rest and ready to be re-energized for another pulse to deliver the liquid drug to a user.

In contrast to the embodiment shown in FIGS. 2-7, the plunger flexure snaps 9 and hard stop flexures 8a and hard stop flexure snaps 8 may be optional as other means of limiting travel of the plunger 3 are available. For example, in FIG. 8, the intermediate pumping chamber may limit itself hydraulically. In addition, in some configurations or applications (e.g., pumping applications that last longer than a use cycle of a drug delivery device for insulin) the use of flexure snaps may induce higher frictional losses, which may be intolerable for a long duration (e.g., greater than 1 week) of use.

Figure 8:
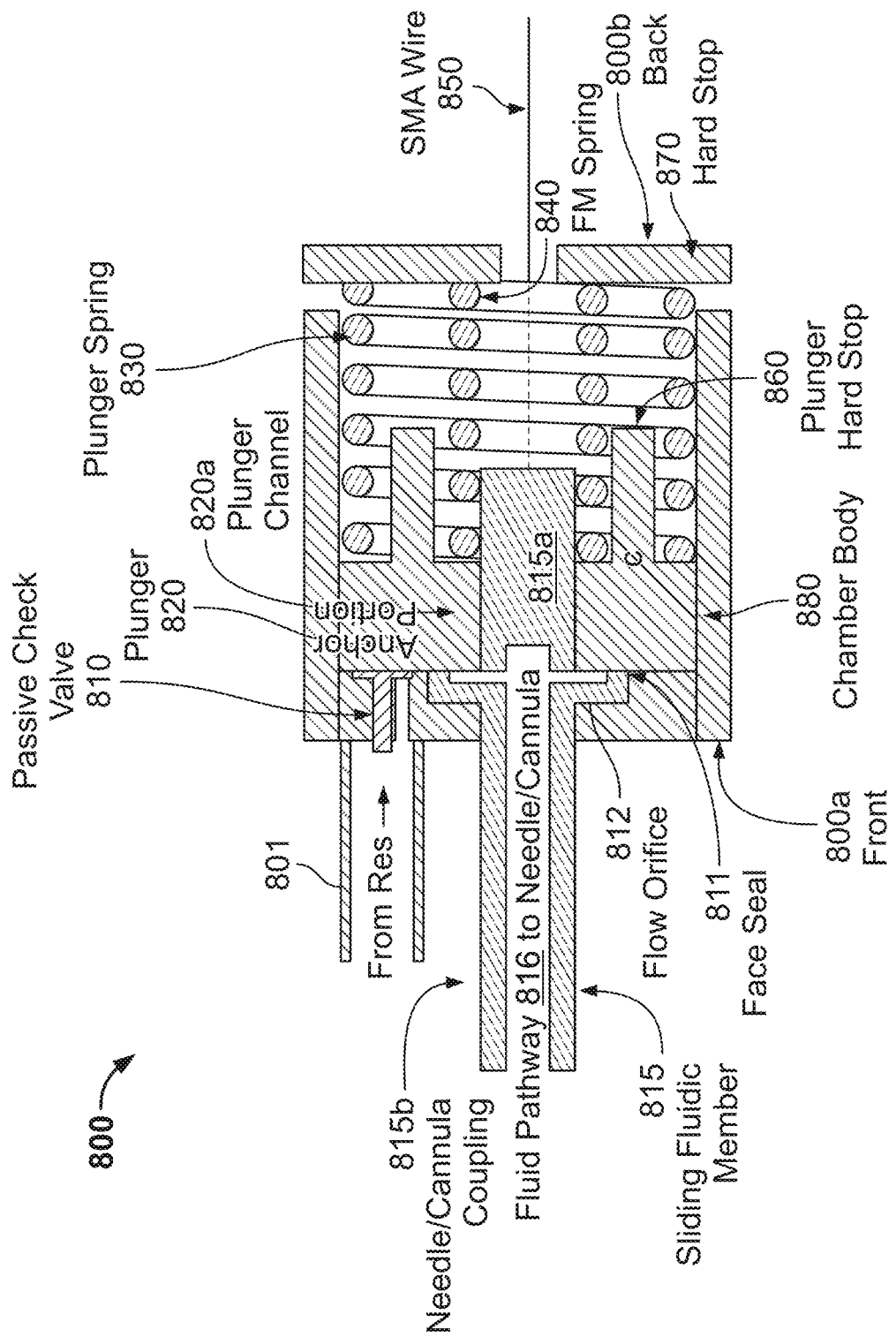
FIG. 8 illustrates a cross-sectional view of another example architecture of an intermediate pumping chamber.

FIG. 8 illustrates a side cross sectional view of another example of intermediate pumping chamber of a wearable drug delivery system. The intermediate pumping chamber 800 may have a front 800a and a back 800b and be coupled to a reservoir containing a liquid drug via reservoir coupling 801. The intermediate pumping chamber 800 may be operable to change configurations over the course of operation. For example, the initial position of FIG. 8 may be a position in which a liquid drug from the reservoir has not been pulled into the pump chamber (shown in more detail in a later figure). The main components of the example intermediate pumping chamber 200 may include sliding fluidic member 815, chamber body 880, and plunger 820. Additional components may include a passive check valve 810, a plunger spring 830, a fluidic member (FM) spring 840, a shape memory alloy (SMA) wire 850, a hard stop 870 and a face seal 811. The plunger spring 830 and the FM spring 840 may, for example, be compression springs and are shown in their rest position when the intermediate pumping chamber 800 is in this initial position. The initial position of the plunger 820 and the sliding fluid member 815 shown in the example of FIG. 8 may also be referred to as the parked position at the front 800a of the intermediate pumping chamber 800. Of course, other types of springs or other types of devices may be used in place of springs in the example intermediate pumping chamber 800.

The sliding fluidic member 815 may be configured with an anchor portion 815a, a needle/cannula coupling 815b, and a flow orifice 812. The sliding fluidic member 815 may include a flow orifice 812 that is built into the sliding fluidic member 815. The sliding fluidic member 1 may be coupled to the needle or cannula, such as 129 of FIG. 1. The anchor portion 815a may include structures (not shown for ease of illustration in this example) that connect to the needle/cannula coupling 815b. The structures are configured to provide fluid passages in the flow orifice 812 that allow the liquid drug to enter the flow orifice and flow in the fluid pathway 816 to the needle/cannula.

In the example intermediate pumping chamber 800, the passive check valve 810 may be configured to prevent back-flow of the liquid drug when the pump chamber is filled with liquid drug (shown in a later example) from the reservoir (shown in FIG. 1).

The plunger 820 may be configured to form a leakproof seal against the side of the chamber body 880. The plunger 820 as shown in later examples is operable to draw liquid drug from the reservoir and deliver the liquid drug through the fluid pathway 816 to the needle or cannula (not shown in this example). A surface of the plunger 820 facing the rear 800b of the intermediate pumping chamber 800 may be coupled to, or sit against, a plunger spring 830. The end of the plunger spring 830 opposite the plunger 820 may couple to, or rest against, the hard stop 870.

In this example, the plunger 820 is configured with a plunger channel 820a and plunger hard stop 860. The plunger channel 820a may be a hollow center portion in which fits an anchor portion 815a of the sliding fluidic member 815. The plunger channel 820a may be configured to surround the anchor portion 815a of the sliding fluidic member 815. The interface between the plunger channel 3a and the anchor portion 1a is leakproof, but the anchor portion 1a is configured to slide back and forth through the plunger channel 820a.

A face seal 811 may be disposed between the plunger 820 and the needle/cannula coupling 815b of the sliding fluidic member 815 to provide a leakproof seal. The face seal 811 may be formed as a compression seal between the sliding fluidic member 815 and a surface of the plunger 820. Alternatively, or in addition, the face seal 811 may be an elastomeric seal coupled to the sliding fluidic member 815 (or the plunger 820). The face seal 811 may be configured to limit leakage of any liquid drug through or around a flow orifice 812 and into the fluid pathway 16 to the needle or cannula. The face seal 811 may be further configured to prevent flow of the liquid drug to the patient while the intermediate pumping chamber is in the initial position. In some stages of operation, the face seal 811 may, for example, be under pressure from the plunger spring 830 of the intermediate pumping chamber 800 that prevents any liquid drug from entering the fluid pathway 816.

The SMA wire 850 may be nitinol or other known shape memory alloy wire that is operable to change length or shape in response to application of a current. For example, the SMA wire 850 may be coupled to a power source via circuitry that, when actuated in response to a control signal from a controller (such as shown in FIG. 1), is configured to apply a current or voltage to actuate the SMA wire 850. The hard stop 870 may be configured to limit movement of the plunger 820 when the hard stop 870 is contacted by the plunger hard stop 860.

Figure 9:
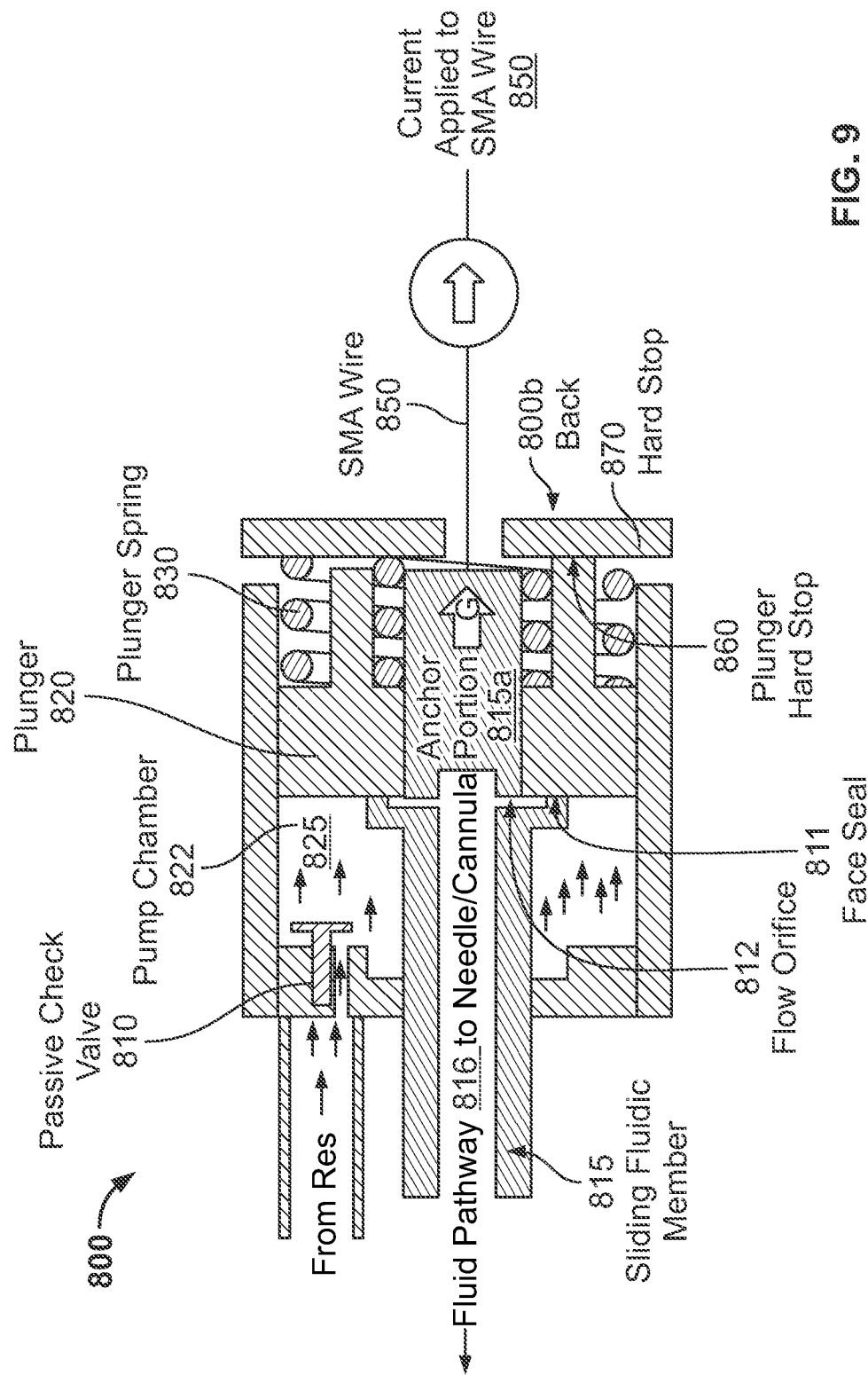
FIG. 9 illustrates a side cross-sectional view of an intermediate pumping chamber of the delivery pump device in transition from an initial state of a pumping cycle for the intermediate pumping chamber shown in the example of FIG. 8.

FIG. 9 illustrates a side cross-sectional view of an intermediate pumping chamber of the delivery pump device in transition from an initial state of a pumping cycle for the intermediate pumping chamber shown in the example of FIG. 8. In the example of FIG. 9, the SMA wire 850 may be energized (or actuated) by a controller. In response to being energized or actuated, the SMA wire 850 may begin pulling (toward the back 800b in the direction shown by arrow G) the anchor portion 815a of the sliding fluidic member 815 toward the back 800b of the intermediate pumping chamber 800.

As the anchor portion 815*a* is pulled toward the back 800*b*, the plunger spring 830 and the FM spring 840 are compressed from their resting positions. In addition, a vacuum is created that draws liquid drug 825 from the reservoir via the reservoir coupling 801 into pump chamber 822. The face seal 811 maintains pressure against the plunger 820 as the anchor portion 815*a* is pulled toward the back 800*b* by SMA wire 850, thereby preventing the liquid drug from entering the flow orifice 812.

Figure 10:
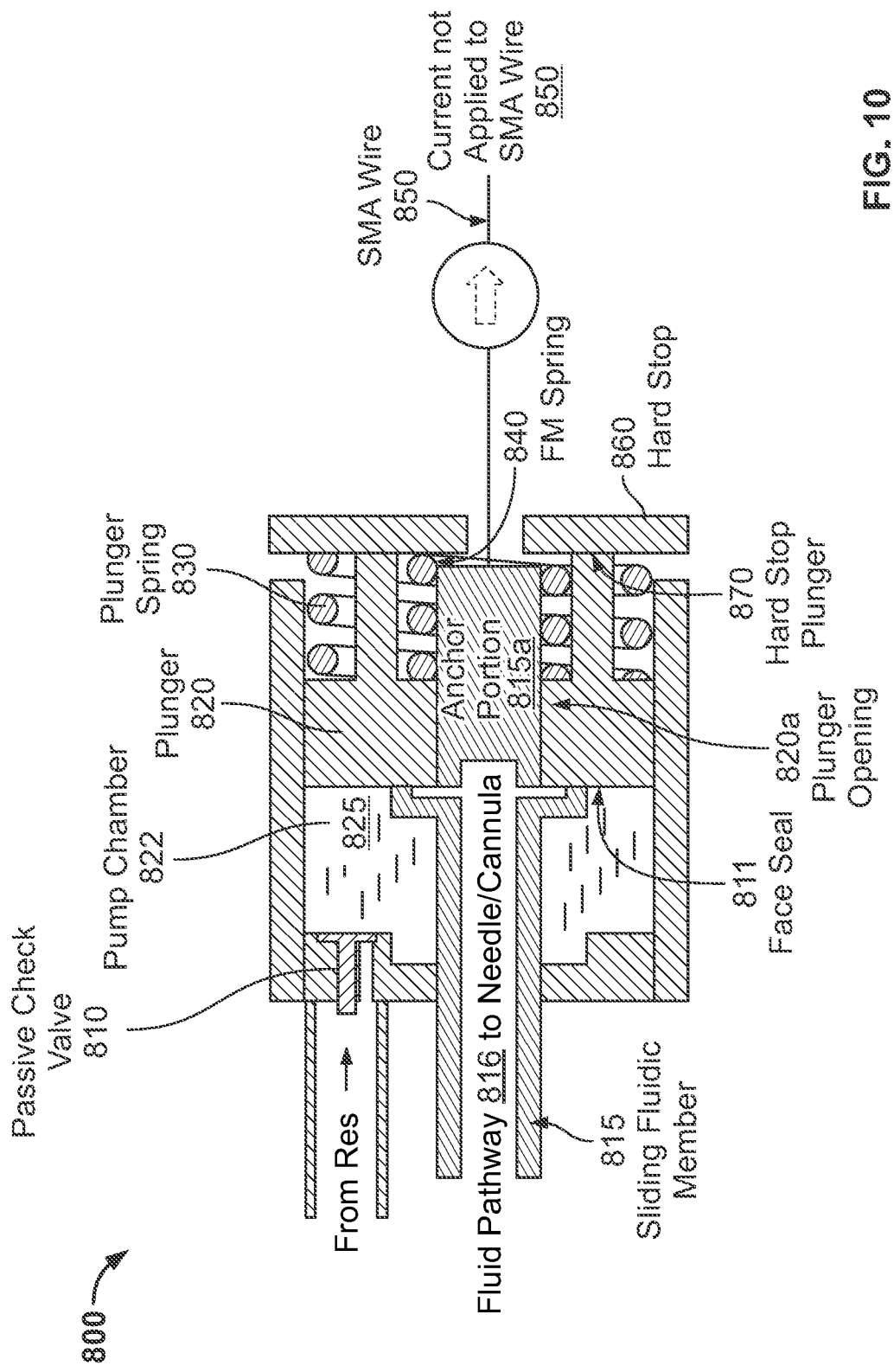
FIG. 10 illustrates a side cross-sectional view of the intermediate pumping chamber in the example of FIG. 9 in a filled state prior to delivery of the liquid drug from the pump chamber.

FIG. 10 illustrates a side cross-sectional view of the intermediate pumping chamber in the example of FIG. 9 in a filled state prior to delivery of the liquid drug from the pump chamber. In the example of FIG. 10, the controller (not shown in this example) no longer causes a current to be applied to the SMA wire 850.

When current is removed from the SMA wire 850, a force imparted by the FM spring 840 may begin to cause reverse motion of the anchor portion 815*a* of the sliding fluidic member 815. The anchor portion 815*a* may begin traveling within the plunger 820 and through the plunger channel 820*a* while the plunger 820 is momentarily hydraulically stalled in position (by the incompressible volume of the liquid drug 825) against the hard stop 860 due to the plunger's greater surface area vis a vis a portion of the surface area of the sliding fluidic member opposite the face seal 811.

In the example of FIG. 10, the SMA wire 850 may be energized by a controller, for example, until a current spike is detected by the controller when the plunger hard stop 860 hits the wall formed by hard stop 870. The timing of the release of the plunger 820, in the example, may be regulated by hydraulic damping due to the liquid drug 825 in the filled pump chamber 822 and the pull exerted on the anchor portion 815*a* by the energized SMA wire 850.

Since the sliding fluidic member 815 is not displacing fluid during movement toward the front 800*a*, there may be no additional force preventing the sliding fluidic member 815 from achieving a "parked position" before the plunger 820 begins to move toward the front 800*a*. Upon movement of the plunger 820, all the liquid drug 825 may be expelled from the pumping chamber 822.

Figure 11:
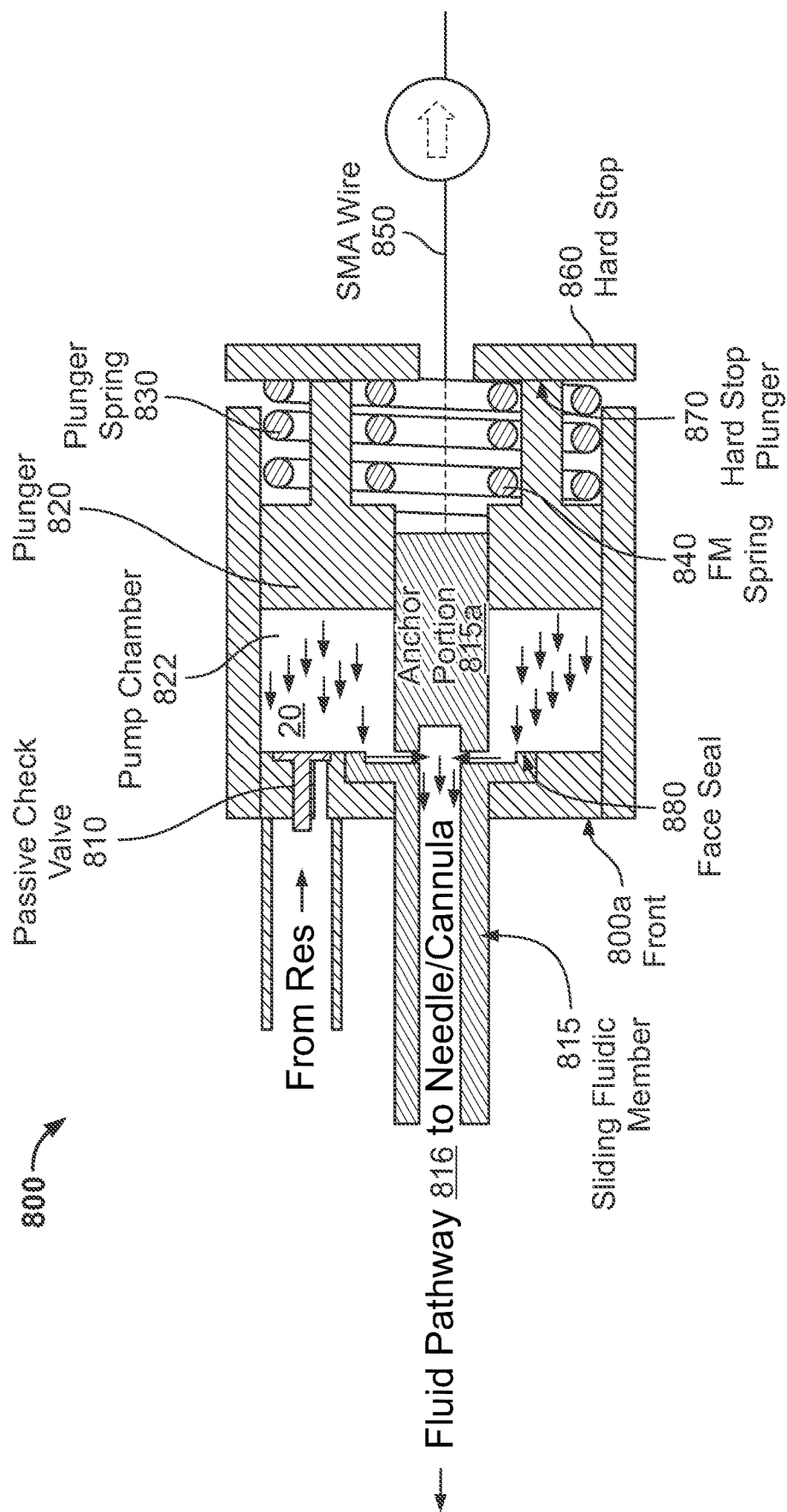
FIG. 11 illustrates a cross-sectional view of the example intermediate pumping chamber transitioning from the filled state of the example of FIG. 4 to a delivery state by movement of the plunger which delivers the liquid drug from the pump chamber.

FIG. 11 illustrates a cross-sectional view of the example intermediate pumping chamber transitioning from the filled state of the example of FIG. 4 to a delivery state.

Based on a spring rate of the FM spring 840, surface area of the plunger contacting the fluid, viscosity of fluid and flow orifice 12 parameters, fluid pathway 816 parameters, and the like, the plunger 820, in the example of FIG. 11, may begin traveling toward the parked position at the front 800*a* before the sliding fluidic member 815 reaches the parked position against the front 800*a* of the intermediate pumping chamber 800. In FIG. 11, the sliding fluidic member 815 is shown in the parked position against the front 800*a* of the intermediate pumping chamber 800. The plunger spring 830 applies force to the plunger 820 that causes the plunger 820 to move toward the front 800*a*. As the plunger 820 is moving and the flow orifice 812 is no longer sealed by the face seal 811, the liquid drug 825 is expelled from the pump chamber 822 by the movement of the plunger 820 toward the front 800*a* of the of the intermediate pumping chamber 800.

When the plunger spring 830 returns to its initial position or parked position as shown in the FIG. 8, the intermediate pumping chamber 800 may be ready and waiting for another pulse.

Figure 12:
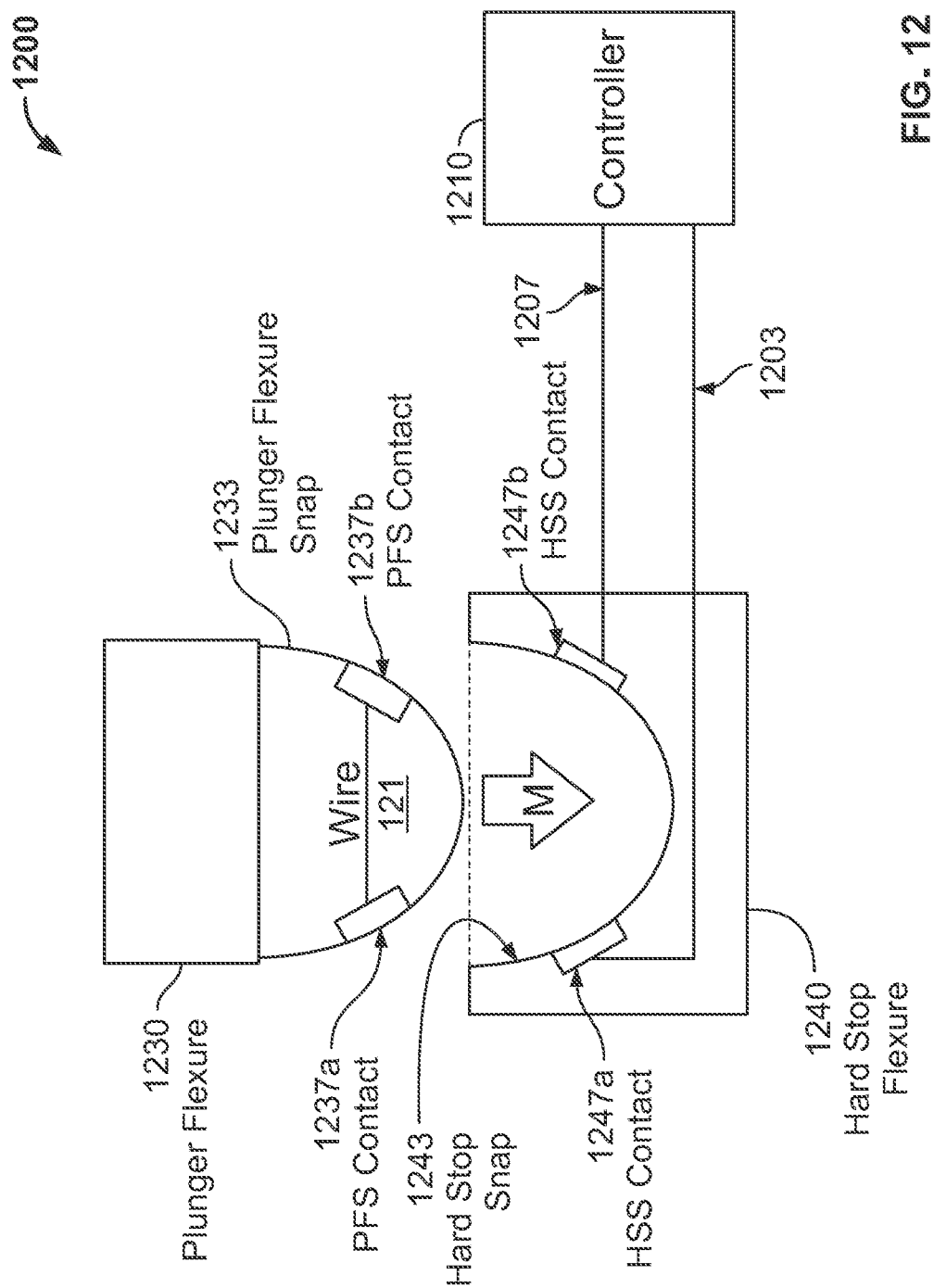
FIG. 12 illustrates an example configuration of electrical contacts for various control aspects of an example of a delivery pump device.

FIG. 12 illustrates an example configuration of electrical contacts for various control aspects of the delivery pump device.

The example configuration 1200 shows examples of a plunger flexure 1230, a hard stop flexure 1240 and a controller 1210.

The plunger flexure 1230 may include the plunger flexure snap 1233. The plunger flexure snap 1233 may be a protrusion disposed at the end of the plunger flexure 1230 as shown in earlier embodiment of FIGS. 2-7. The plunger flexure snap 1233 may include plunger flexure snap (PFS) contacts 1237*a* and 1237*b* that are coupled together by a wire 121.

The hard stop flexure 1240 may include a hard stop snap 1243. Disposed within the hard stop flexure snap 1243 are hard stop snap (HSS) contacts 1247*a* and 1247*b*. The hard stop flexure snap 1243 may be a dimple, or bowl-shaped indent, in the hard stop flexure 1240 as shown in the earlier embodiment of FIGS. 2-7. The HSS contacts 1247*a* and 1247*b* are shown coupled via wired connections to a controller 1210 of a drug delivery device, such as 104 in the example of FIG. 1. The plunger flexure snap 1233 is configured to interact with the hard stop snap 1243. Of course, the plunger flexure snap 1233 and the hard stop snap 1243 may have other shapes that enable coupling of the respective snaps 1233 and 1243.

The controller 1210 may be coupled to HSS contact 1247*a* via connector 1203 and to HSS contact 1247*b* by connector 1207. The controller 1210 may be operable to respond when plunger flexure snap 1233 moves in the direction of arrow M and PSF contacts 1237*a* and 1237*b* contact HSS contacts 1247*a* and 1247*b*, respectively. Upon making contact, a circuit is completed in the controller 1210, which indicates that the plunger has reached the hard stop of the intermediate pumping chamber (shown in earlier examples). In the example of 1200, electrical contacts are shown as examples; however, other devices and mechanisms may be used to determine a status of the drug delivery device, such as 105 of FIG. 1, such as additional electrical switches and interconnects, optical devices coupled to the controller and configured to indicate positions of the plunger, magnetic/eddy current detectors, capacitive and fluid detection devices coupled to various components within a pump chamber, a linear variable displacement transducer (LVDT) or other linear displacement measuring tool, a pressure sensor, a flow sensor on an inlet or a Bourdon tube. The Bourdon tube, for example, may be configured to detect pressure causing strain or deformation in tubing, such as the fluid pathway 16 or 816. The flow sensor, for example, may be operable to respond to check valve leakage or backflow.

Figure 13:
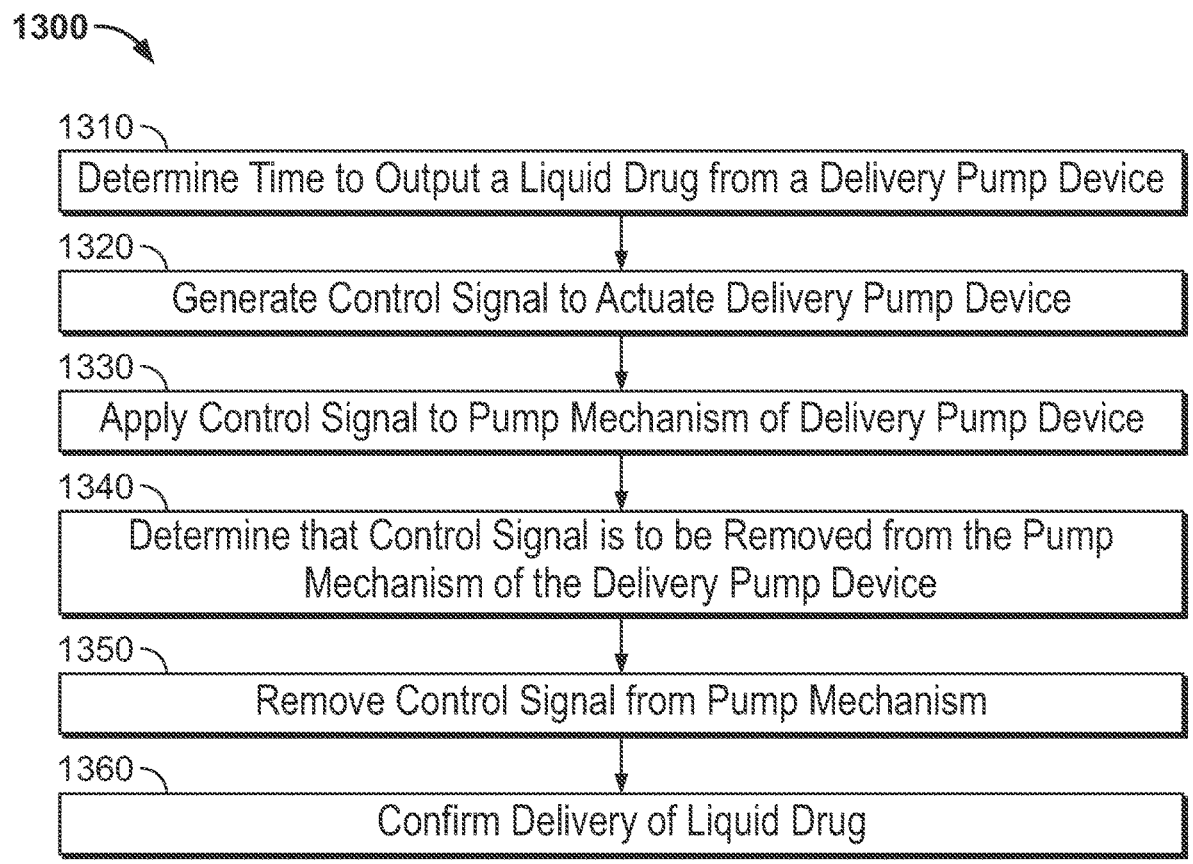
FIG. 13 is a flow chart of a process that may utilize the examples of FIGS. 1-12 to expel a drug from a delivery pump device.

In another example, a controller, such as 102 of FIG. 1 or 1210 of FIG. 12, may be configured to execute logic that causes the controller to perform different functions. FIG. 13 is a flow chart of a process that may utilize the examples of FIGS. 1-12 to expel a drug from a delivery pump device.

In the process 1300, for example, the controller may determine that it is time to output a drug from the delivery pump device. For example, the controller may be equipped with a clock or an input device that indicates to the controller that a dose of medication is supposed to be delivered to a user (1310).

In response to the determination, the controller may generate a control signal to actuate delivery pump device (1320). The controller may be operable to output the control signal, for example, to a pump mechanism that is operable to move the sliding fluidic member as described with reference to the examples of FIGS. 2-11.

In the example, the controller may be operable to apply the control signal to the pump mechanism (1330). The pump mechanism may be a shape memory alloy wire (as described with reference to earlier examples) or an electric motor. In some examples, the intermediate pumping chamber and associated mechanisms may include a drive system coupled to the sliding fluidic member (shown in the examples of FIGS. 2-11). The drive system may, for example, be configured to be moved by a rotary cam, a linkage, a rack, or a leadscrew with an escapement mechanism. In another specific example, the drive system may be geared to allow use of low power electric motors.

As the control signal is being applied to the pump mechanism, the pump chamber (shown in earlier examples) is being filled with a liquid drug. As described with reference to the earlier examples, a shape memory wire is used to pull the sliding fluidic member to enable filling of the pump chamber.

The controller may, for example, be configured to determine that the control signal is to be removed from the pump mechanism of the delivery pump device (1340). The determination may be made as described with reference to the example configuration shown in FIG. 12. As an alternative example, the sliding fluidic member may be magnetically energized, and an eddy current can be measured and evaluated to determine a proximity of the sliding fluidic member to the hard stop wall. The eddy current configuration may allow partial dosing or multi-dosing within the same intermediate pumping chamber as the eddy current may have different values as the sliding fluidic member travels. Of course, other methods or placements of electrical contacts may be used to determine the position of the sliding fluidic member within the intermediate pumping chamber. Upon determining that the control signal may be removed from the pump mechanism, the controller may, at 1350, stop applying or having applied a signal (responsive to the control signal) the drive mechanism, such as the shape memory alloy. By stopping the application of the control signal, the controller enables the springs of the intermediate pumping chamber to begin expelling the liquid drug from the pump chamber and to the patient via the fluid pathway to the needle/cannula. For example, the expelling of the liquid drug may enable delivery of the liquid drug from the drug delivery device.

In an operational example, the delivery of the liquid drug to a needle or cannula in response to removing the control signal from the pump mechanism may include additional steps. For example, in response to the shape memory alloy stopping pulling of the sliding fluidic member, the fluidic member spring may begin decompressing. The decompressing fluidic member spring may cause the sliding fluidic member to travel toward the front of the chamber body, while the plunger remains stationary due to being hydraulically blocked by the liquid drug in the pump chamber. The liquid drug is incompressible which counteracts the force exerted by the plunger spring until such time as the sliding fluidic member reaches a rest position or initial position as shown in the example of FIG. 2. In the example, the flow orifice is available to enable the liquid drug to flow into the needle coupling upon the sliding fluidic member reaching the initial position. With the sliding fluidic member is at the initial position or rest position, the plunger spring begins to decompress causing liquid drug to be expelled from the pump chamber into the needle coupling.

The controller may be operable, at 1360, to confirm that the liquid drug was delivered or expelled, or has begun to be delivered or expelled, from the pumping chamber. For example, the sliding fluidic member may include electrical contacts or the like, such as the earlier eddy current example.

The whole system can be moved by sealing the back side of the plunger/sliding fluidic member and drawing a vacuum using a small air pump. The system would allow pressure to be measured in the vacuum chamber and through a calculation using Boyles Law ($P_1V_1=P_2V_2$), the position of the plunger can be established.

The system may be modified to utilize phase changing wax in the movement of the plunger in place of the shape memory alloy as described in U.S. Pat. No. 10,391,237, the disclosure of which is incorporated by reference in its entirety herein.

Software related implementations of the techniques described herein may include, but are not limited to, firmware, application specific software, or any other type of computer readable instructions that may be executed by one or more processors. Hardware related implementations of the techniques described herein may include, but are not limited to, integrated circuits (ICs), application specific ICs (ASICs), field programmable arrays (FPGAs), and/or programmable logic devices (PLDs). In some examples, the techniques described herein, and/or any system or constituent component described herein may be implemented with a processor executing computer readable instructions stored on one or more memory components.

In addition, or alternatively, while the examples may have been described with reference to a closed loop algorithmic implementation, variations of the disclosed examples may be implemented to enable open loop use. The open loop implementations allow for use of different modalities of delivery of insulin such as smart pen, syringe or the like. For example, the disclosed AP application and algorithms may be operable to perform various functions related to open loop operations, such as the generation of prompts requesting the input of information such as weight or age. Similarly, a dosage amount of insulin may be received by the AP application or algorithm from a user via a user interface. Other open-loop actions may also be implemented by adjusting user settings or the like in an AP application or algorithm.

Some examples of the disclosed device may be implemented, for example, using a storage medium, a computer-readable medium, or an article of manufacture which may store an instruction or a set of instructions that, if executed by a machine (i.e., processor or microcontroller), may cause the machine to perform a method and/or operation in accordance with examples of the disclosure. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory, memory article, memory medium, storage device, storage article, storage medium and/or storage unit, for example, memory (including non-transitory memory), removable or non-removable media, erasable or non-erasable media, writable or re-writable media, digital or analog media, hard disk, floppy disk, Compact Disk Read Only Memory (CD-ROM), Compact Disk Recordable (CD-R), Compact Disk Rewritable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, programming code, and the like, implemented using any suitable high-level, low-level, object-oriented, visual, compiled and/or interpreted programming language. The non-transitory computer readable medium embodied programming code may cause a processor when executing the programming code to perform functions, such as those described herein.

Certain examples of the present disclosure were described above. It is, however, expressly noted that the present disclosure is not limited to those examples, but rather the intention is that additions and modifications to what was expressly described herein are also included within the scope of the disclosed examples. Moreover, it is to be understood that the features of the various examples described herein were not mutually exclusive and may exist in various combinations and permutations, even if such combinations or permutations were not made express herein, without departing from the spirit and scope of the disclosed examples. In fact, variations, modifications, and other implementations of what was described herein will occur to those of ordinary skill in the art without departing from the spirit and the scope of the disclosed examples. As such, the disclosed examples are not to be defined only by the preceding illustrative description.

Program aspects of the technology may be thought of as "products" or "articles of manufacture" typically in the form of executable code and/or associated data that is carried on or embodied in a type of non-transitory, machine readable medium. Storage type media include any or all of the tangible memory of the computers, processors or the like, or associated modules thereof, such as various semiconductor memories, tape drives, disk drives and the like, which may provide non-transitory storage at any time for the software programming. It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single example for streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example. In the appended claims, the terms "including" and "in which" are used as the plain-English equivalents of the respective terms "comprising" and "wherein," respectively. Moreover, the terms "first," "second," "third," and so forth, are used merely as labels and are not intended to impose numerical requirements on their objects.

The foregoing description of examples has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future filed applications claiming priority to this application may claim the disclosed subject matter in a different manner and may generally include any set of one or more limitations as variously disclosed or otherwise demonstrated herein.

What is claimed is:

1. A wearable drug delivery device, comprising:
    a reservoir configured to store a liquid drug; and
    a delivery pump device coupled to the reservoir for receiving the liquid drug from the reservoir, the delivery pump device comprising:
        a chamber body defining a pump chamber,
        an inlet port configured to enable a liquid drug from the reservoir to be drawn into the pump chamber,
        a sliding fluidic member including a flow orifice and a fluid pathway to a needle,
        a plunger including a plunger channel configured to be engaged with the sliding fluidic member, and
        a shape memory alloy wire coupled to the sliding fluidic member,
    wherein:
        the shape memory alloy wire is operable to draw the liquid drug from the reservoir through the inlet port and into the pump chamber by pulling the sliding fluidic member and the plunger in a first direction, and
        the sliding fluidic member is configured to enable the liquid drug to be drawn into the pump chamber and expelled from the pump chamber into a fluid pathway to a needle for output.

2. The wearable drug delivery device of claim 1, wherein the sliding fluidic member further comprises:
    a face seal that is configured to maintain a fluid-proof seal against a first plunger surface of the plunger as the shape memory alloy wire pulls an anchor portion.

3. The wearable drug delivery device of claim 1, wherein the sliding fluidic member further comprises:
    an anchor portion coupled to the shape memory alloy wire, wherein the anchor portion is configured to engage the plunger by traversing into a plunger channel of the plunger in response to the pull by the shape memory alloy wire; and
    a needle coupling connected to an anchor portion.

4. The wearable drug delivery device of claim 1, wherein the plunger is configured to make direct physical contact with an interior surface of the chamber body to define the pumping chamber.

5. The wearable drug delivery device of claim 1, further comprising:
    a fluidic member spring having a first end coupled to an anchor portion; and
    a plunger spring having a first end coupled to the plunger,
    wherein the fluidic member spring and the plunger spring are configured to be pulled from a rest position to a compressed position by the shape memory alloy wire.

6. The wearable drug delivery device of claim 1, further comprising:
    a hard stop opposite the inlet port;
    a fluidic member spring having a first end coupled to an anchor portion; and
    a plunger spring having a first end coupled to the plunger,
    wherein the hard stop is configured to contact a second end of the plunger spring, opposite the first end of the plunger spring and further configured to contact a second end of the fluidic member spring, opposite the first end of the fluidic member spring coupled to the plunger.

7. The wearable drug delivery device of claim 6, wherein:
    the hard stop further includes a hard stop flexure snap; and
    the plunger further includes a plunger flexure snap,
    wherein the plunger flexure snap and the hard stop flexure snap are configured to engage one another as the shape memory alloy wire pulls the anchor portion.

8. The wearable drug delivery device of claim 1, wherein the inlet port further comprises a passive check valve.

9. The wearable drug delivery device of claim 1, further comprising:
a power source coupled to the shape memory alloy, wherein power from the power source is applied to the shape memory alloy to cause the shape memory wire to contract and thereby pull an anchor portion.

10. The wearable drug delivery device of claim 6, further comprising a controller communicatively coupled to a power source, wherein the controller is operable to:
activate the power source to cause power to be applied to the shape memory alloy in response to an automated insulin delivery application setting.

11. A delivery pump device of a wearable drug delivery device, the delivery pump device comprising:
a chamber body defining a pump chamber, the chamber body including a hard stop and an inlet valve operable to receive a liquid drug from a reservoir;
a plunger movable within the pump chamber of the chamber body and configured with a plunger channel;
a sliding fluidic member movable within the pump chamber and including a needle coupling, a flow orifice, a face seal and an anchor portion, wherein the anchor portion is positioned and movable within the plunger channel in a leak-proof configuration; and
a shape memory alloy wire coupled to the anchor portion, wherein the shape memory alloy wire is operable to pull the anchor portion and the plunger toward the hard stop.

12. The delivery pump device of claim 11, wherein the face seal is configured to maintain a leak-proof seal against a first surface of the plunger to form the leak-proof configuration.

13. The delivery pump device of claim 11, the plunger further comprising:
a plunger hard stop that is configured to engage the hard stop of the housing; and
a plunger spring, wherein the plunger spring is in a compressed position when the plunger hard stop engages the hard stop of the chamber body.

14. The delivery pump device of claim 11, wherein the shape memory alloy wire is configured to:
pull the sliding fluidic member and the plunger in a first direction away from a front of the chamber body in response to application of a current to the shape memory alloy wire, wherein the liquid drug is drawn from the reservoir through the inlet valve into the pump chamber; and
stop pulling the sliding fluidic member and the plunger in response to the current no longer being applied to the shape memory wire, wherein the pump chamber is filled with the liquid drug.

15. The delivery pump device of claim 14, further comprising:
a plunger spring; and
a fluidic member spring,
wherein:
the plunger spring is configured to contact a hard stop of the chamber body,
the fluidic member spring is configured to contact the hard stop of the chamber body, and
when the shape memory alloy wire stops pulling the sliding fluidic member, the plunger spring and the fluidic member spring are compressed.

16. The delivery pump device of claim 15, wherein the delivery pump device is further configured to:
in response to the shape memory alloy stopping pulling the sliding fluidic member, the fluidic member spring begins decompressing causing the sliding fluidic member to travel toward the front of the chamber body, while the plunger remains stationary due to being hydraulically blocked by the liquid drug in the pump chamber.

17. The delivery pump device of claim 16, wherein the delivery pump device is further configured to:
upon the sliding fluidic member reaching an initial position, the flow orifice is available to enable the liquid drug to flow into the needle coupling; and
the plunger spring begins to decompress causing liquid drug to be expelled from the pump chamber into the needle coupling.

18. The wearable drug delivery device of claim 10, further comprising:
a first fluid path component connecting the reservoir with an inlet port of the housing; and
a second fluid path component connecting an outlet port of the housing with a cannula, wherein the inlet valve is positioned within the inlet port, and wherein the outlet valve is positioned within the outlet port.

* * * * *